(12) United States Patent
Lindner et al.

(10) Patent No.: US 11,119,054 B2
(45) Date of Patent: Sep. 14, 2021

(54) VERSATILE DISPLAY SCAFFOLDS FOR PROTEINS

(71) Applicant: THE PENN STATE RESEARCH FOUNDATION, University Park, PA (US)

(72) Inventors: Scott Eugene Lindner, State College, PA (US); Susan Hafenstein, Lemont, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 16/494,502

(22) PCT Filed: Mar. 16, 2018

(86) PCT No.: PCT/US2018/022803
§ 371 (c)(1),
(2) Date: Sep. 16, 2019

(87) PCT Pub. No.: WO2018/170362
PCT Pub. Date: Sep. 20, 2018

(65) Prior Publication Data
US 2020/0124544 A1    Apr. 23, 2020

Related U.S. Application Data

(60) Provisional application No. 62/472,119, filed on Mar. 16, 2017.

(51) Int. Cl.
*G01N 23/04*    (2018.01)
*C07K 1/00*     (2006.01)
*C07K 14/47*    (2006.01)

(52) U.S. Cl.
CPC .......... *G01N 23/04* (2013.01); *C07K 1/00* (2013.01); *C07K 14/47* (2013.01); *C07K 2319/23* (2013.01); *C07K 2319/50* (2013.01); *C07K 2319/80* (2013.01); *G01N 2223/612* (2013.01)

(58) Field of Classification Search
CPC ...... C07K 14/47; C07K 14/4702; C07K 1/00; C07K 2319/21; C07K 2319/22; C07K 2319/23; C07K 2319/50; C07K 2319/80; C07K 2319/85; G01N 2223/102; G01N 2223/612; G01N 23/04; G16B 15/00
See application file for complete search history.

(56) References Cited

U.S. PATENT DOCUMENTS

| | | | |
|---|---|---|---|
| 9,630,994 B2 * | 4/2017 | Baker | C07K 14/00 |
| 10,351,603 B2 * | 7/2019 | Baker | C07K 14/00 |
| 2020/0017556 A1 * | 1/2020 | Howorka | C12Q 1/6869 |

FOREIGN PATENT DOCUMENTS

| | | |
|---|---|---|
| WO | 2016/138525 A1 | 9/2016 |
| WO | 2016/193746 A1 | 12/2016 |

OTHER PUBLICATIONS

Liu et al. Near-atomic cryo-EM imaging of a small protein displayed on a designed scaffolding system . PNAS, Mar. 27, 2018. vol. 115, No. 13, pp. 3362-3367. (Year: 2018).*

Lee et al. A Cryo-Electron Microscopy Study Identifies the Complete H16.V5 Epitope and Reveals Global Conformational Changes Initiated by Binding of the Neutralizing Antibody Fragment. JVI, Jan. 2015, vol. 89, No. 2, pp. 1428-1438. (Year: 2015).*

Guan et al. Structural comparison of four different antibodies interacting with human papillomavirus 16 and mechanisms of neutralization. Virology. Sep. 2015; vol. 483, pp. 253-263. (Year: 2015).*

PBS: https://www.protocolsonline.com/recipes/phosphate-buffered-saline-pbs/, last update Oct. 3, 2016. accessed online Dec. 19, 2020. (Year: 2016).*

Coscia et al., Fusion to a homo-oligomeric scaffold allows cryo-EM analysis of a small protein. Sci Rep, Aug. 3, 2016, vol. 6, No, p. 30909 (pp. 1-11).

Brune et al., Plug-and-Display: deco ration of Virus-Like Particles via isopeptide bonds for modular immunization. Sci Rep, Jan. 19, 2016, vol. 6, p. 19234 (pp. 1-13).

Deo et al., Recognition of polyadenylate RNA by the poly(A)-binding protein. Cell, Sep. 17, 1999, vol. 98, No. 6, pp. 835-845.

* cited by examiner

*Primary Examiner* — Marcela M Cordero Garcia
(74) *Attorney, Agent, or Firm* — Meunier Carlin & Curfman LLC

(57) ABSTRACT

Provided are processes and materials for solving biological or structural information about proteins or other organic molecules. The processes capitalize on a rigid multimeric nanocage formed from self-assembling substructure proteins. The processes and materials allow for recognition and tight, optionally covalent, bonding of any protein molecule with a tag complementary to a capture sequence on the nanocage. The processes and materials may be used to obtain biological or structural information by cryo-electron microscopy and overcome prior limitations of target protein size or salt concentration.

11 Claims, 9 Drawing Sheets

Specification includes a Sequence Listing.

SEQUENCE LISTING

```
<160> NUMBER OF SEQ ID NOS: 29

<210> SEQ ID NO 1
<211> LENGTH: 205
<212> TYPE: PRT
<213> ORGANISM: Artificial Sequence
<220> FEATURE:
<223> OTHER INFORMATION: I3-01 sequence

<400> SEQUENCE: 1

Met Glu Glu Leu Phe Lys Lys His Lys Ile Val Ala Val Leu Arg Ala
1               5                   10                  15

Asn Ser Val Glu Glu Ala Lys Lys Lys Ala Leu Ala Val Phe Leu Gly
            20                  25                  30

Gly Val His Leu Ile Glu Ile Thr Phe Thr Val Pro Asp Ala Asp Thr
        35                  40                  45

Val Ile Lys Glu Leu Ser Phe Leu Lys Glu Met Gly Ala Ile Ile Gly
    50                  55                  60

Ala Gly Thr Val Thr Ser Val Glu Gln Cys Arg Lys Ala Val Glu Ser
65                  70                  75                  80

Gly Ala Glu Phe Ile Val Ser Pro His Leu Asp Glu Glu Ile Ser Gln
                85                  90                  95

Phe Cys Lys Glu Lys Gly Val Phe Tyr Met Pro Gly Val Met Thr Pro
            100                 105                 110

Thr Glu Leu Val Lys Ala Met Lys Leu Gly His Thr Ile Leu Lys Leu
        115                 120                 125

Phe Pro Gly Glu Val Val Gly Pro Gln Phe Val Lys Ala Met Lys Gly
    130                 135                 140

Pro Phe Pro Asn Val Lys Phe Val Pro Thr Gly Gly Val Asn Leu Asp
145                 150                 155                 160

Asn Val Cys Glu Trp Phe Lys Ala Gly Val Leu Ala Val Gly Val Gly
```

```
                165                 170                 175
Ser Ala Leu Val Lys Gly Thr Pro Val Glu Val Ala Glu Lys Ala Lys
            180                 185                 190

Ala Phe Val Glu Lys Ile Arg Gly Cys Thr Glu His Met
        195                 200                 205

<210> SEQ ID NO 2
<211> LENGTH: 205
<212> TYPE: PRT
<213> ORGANISM: Artificial Sequence
<220> FEATURE:
<223> OTHER INFORMATION: I3-01 sequence EAAAK-v1

<400> SEQUENCE: 2

Met Glu Glu Leu Phe Lys Lys His Lys Ile Val Ala Val Leu Arg Ala
1               5                   10                  15

Asn Ser Val Glu Glu Ala Lys Lys Lys Ala Leu Ala Val Phe Leu Gly
            20                  25                  30

Gly Val His Leu Ile Glu Ile Thr Phe Thr Val Pro Asp Ala Asp Thr
        35                  40                  45

Val Ile Lys Glu Leu Ser Phe Leu Lys Glu Met Gly Ala Ile Ile Gly
    50                  55                  60

Ala Gly Thr Val Thr Ser Val Glu Gln Cys Arg Lys Ala Val Glu Ser
65                  70                  75                  80

Gly Ala Glu Phe Ile Val Ser Pro His Leu Asp Glu Glu Ile Ser Gln
                85                  90                  95

Phe Cys Lys Glu Lys Gly Val Phe Tyr Met Pro Gly Val Met Thr Pro
            100                 105                 110

Thr Glu Leu Val Lys Ala Met Lys Leu Gly His Thr Ile Leu Lys Leu
        115                 120                 125

Phe Pro Gly Glu Val Val Gly Pro Gln Phe Val Lys Ala Met Lys Gly
    130                 135                 140

Pro Phe Pro Asn Val Lys Phe Val Pro Thr Gly Gly Val Asn Leu Asp
145                 150                 155                 160

Asn Val Cys Glu Trp Phe Lys Ala Gly Val Leu Ala Val Gly Val Gly
                165                 170                 175

Ser Ala Leu Val Lys Gly Thr Pro Val Glu Val Ala Glu Lys Ala Lys
            180                 185                 190

Ala Phe Val Glu Lys Ile Arg Gly Cys Thr Glu His Met
        195                 200                 205

<210> SEQ ID NO 3
<211> LENGTH: 201
<212> TYPE: PRT
<213> ORGANISM: Artificial Sequence
<220> FEATURE:
<223> OTHER INFORMATION: I3-01 sequence EAAAK-v2, 9x-Pro, and 3xPPA

<400> SEQUENCE: 3

Phe Lys Lys His Lys Ile Val Ala Val Leu Arg Ala Asn Ser Val Glu
1               5                   10                  15

Glu Ala Lys Lys Lys Ala Leu Ala Val Phe Leu Gly Gly Val His Leu
            20                  25                  30

Ile Glu Ile Thr Phe Thr Val Pro Asp Ala Asp Thr Val Ile Lys Glu
        35                  40                  45

Leu Ser Phe Leu Lys Glu Met Gly Ala Ile Ile Gly Ala Gly Thr Val
    50                  55                  60
```

```
Thr Ser Val Glu Gln Cys Arg Lys Ala Val Glu Ser Gly Ala Glu Phe
 65                  70                  75                  80

Ile Val Ser Pro His Leu Asp Glu Glu Ile Ser Gln Phe Cys Lys Glu
                 85                  90                  95

Lys Gly Val Phe Tyr Met Pro Gly Val Met Thr Pro Thr Glu Leu Val
            100                 105                 110

Lys Ala Met Lys Leu Gly His Thr Ile Leu Lys Leu Phe Pro Gly Glu
            115                 120                 125

Val Val Gly Pro Gln Phe Val Lys Ala Met Lys Gly Pro Phe Pro Asn
            130                 135                 140

Val Lys Phe Val Pro Thr Gly Val Asn Leu Asp Asn Val Cys Glu
145                 150                 155                 160

Trp Phe Lys Ala Gly Val Leu Ala Val Gly Val Gly Ser Ala Leu Val
                165                 170                 175

Lys Gly Thr Pro Val Glu Val Ala Glu Lys Ala Lys Ala Phe Val Glu
            180                 185                 190

Lys Ile Arg Gly Cys Thr Glu His Met
            195                 200

<210> SEQ ID NO 4
<211> LENGTH: 207
<212> TYPE: PRT
<213> ORGANISM: Artificial Sequence
<220> FEATURE:
<223> OTHER INFORMATION: I3-01 sequence

<400> SEQUENCE: 4

Met Lys Met Glu Glu Leu Phe Lys Lys His Lys Ile Val Ala Val Leu
  1               5                  10                  15

Arg Ala Asn Ser Val Glu Glu Ala Lys Lys Lys Ala Leu Ala Val Phe
                 20                  25                  30

Leu Gly Gly Val His Leu Ile Glu Ile Thr Phe Thr Val Pro Asp Ala
            35                  40                  45

Asp Thr Val Ile Lys Glu Leu Ser Phe Leu Lys Glu Met Gly Ala Ile
 50                  55                  60

Ile Gly Ala Gly Thr Val Thr Ser Val Glu Gln Cys Arg Lys Ala Val
 65                  70                  75                  80

Glu Ser Gly Ala Glu Phe Ile Val Ser Pro His Leu Asp Glu Glu Ile
                 85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Val Glu Val Ala Glu Lys
            180                 185                 190

Ala Lys Ala Phe Val Glu Lys Ile Arg Gly Cys Thr Glu His Met
            195                 200                 205

<210> SEQ ID NO 5
<211> LENGTH: 206
```

```
<212> TYPE: PRT
<213> ORGANISM: Artificial Sequence
<220> FEATURE:
<223> OTHER INFORMATION: I3-03 sequence EAAAK-v1

<400> SEQUENCE: 5

Ser Met Glu Glu Leu Phe Lys Lys His Lys Ile Val Ala Val Leu Arg
1               5                   10                  15

Ala Asn Ser Val Glu Glu Ala Lys Lys Lys Ala Leu Ala Val Phe Leu
            20                  25                  30

Gly Gly Val His Leu Ile Glu Ile Thr Phe Thr Val Pro Asp Ala Asp
        35                  40                  45

Thr Val Ile Lys Glu Leu Ser Phe Leu Lys Glu Met Gly Ala Ile Ile
    50                  55                  60

Gly Ala Gly Thr Val Thr Ser Val Glu Gln Cys Arg Lys Ala Val Glu
65                  70                  75                  80

Ser Gly Ala Glu Phe Ile Val Ser Pro His Leu Asp Glu Glu Ile Ser
                85                  90                  95

Gln Phe Cys Lys Glu Lys Gly Val Phe Tyr Met Pro Gly Val Met Thr
            100                 105                 110

Pro Thr Glu Leu Val Lys Ala Met Lys Leu Gly His Thr Ile Leu Lys
        115                 120                 125

Leu Phe Pro Gly Glu Val Val Gly Pro Gln Phe Val Lys Ala Met Lys
    130                 135                 140

Gly Pro Phe Pro Asn Val Lys Phe Val Pro Thr Gly Gly Val Asn Leu
145                 150                 155                 160

Asp Asn Val Cys Glu Trp Phe Lys Ala Gly Val Leu Ala Val Gly Val
                165                 170                 175

Gly Ser Ala Leu Val Lys Gly Thr Pro Val Glu Val Ala Glu Lys Ala
            180                 185                 190

Lys Ala Phe Val Glu Lys Ile Arg Gly Cys Thr Glu His Met
        195                 200                 205

<210> SEQ ID NO 6
<211> LENGTH: 204
<212> TYPE: PRT
<213> ORGANISM: Artificial Sequence
<220> FEATURE:
<223> OTHER INFORMATION: I3-03 sequence EAAAK-v2, 9x-Pro, and 3xPPA

<400> SEQUENCE: 6

Glu Glu Leu Phe Lys Lys His Lys Ile Val Ala Val Leu Arg Ala Asn
1               5                   10                  15

Ser Val Glu Glu Ala Lys Lys Lys Ala Leu Ala Val Phe Leu Gly Gly
            20                  25                  30

Val His Leu Ile Glu Ile Thr Phe Thr Val Pro Asp Ala Asp Thr Val
        35                  40                  45

Ile Lys Glu Leu Ser Phe Leu Lys Glu Met Gly Ala Ile Ile Gly Ala
    50                  55                  60

Gly Thr Val Thr Ser Val Glu Gln Cys Arg Lys Ala Val Glu Ser Gly
65                  70                  75                  80

Ala Glu Phe Ile Val Ser Pro His Leu Asp Glu Glu Ile Ser Gln Phe
                85                  90                  95

Cys Lys Glu Lys Gly Val Phe Tyr Met Pro Gly Val Met Thr Pro Thr
            100                 105                 110

Glu Leu Val Lys Ala Met Lys Leu Gly His Thr Ile Leu Lys Leu Phe
        115                 120                 125
```

```
Pro Gly Glu Val Val Gly Pro Gln Phe Val Lys Ala Met Lys Gly Pro
        130                 135                 140

Phe Pro Asn Val Lys Phe Val Pro Thr Gly Gly Val Asn Leu Asp Asn
145                 150                 155                 160

Val Cys Glu Trp Phe Lys Ala Gly Val Leu Ala Val Gly Val Gly Ser
                165                 170                 175

Ala Leu Val Lys Gly Thr Pro Val Glu Val Ala Glu Lys Ala Lys Ala
            180                 185                 190

Phe Val Glu Lys Ile Arg Gly Cys Thr Glu His Met
                195                 200

<210> SEQ ID NO 7
<211> LENGTH: 98
<212> TYPE: PRT
<213> ORGANISM: Artificial Sequence
<220> FEATURE:
<223> OTHER INFORMATION: Spycatcher Sequence

<400> SEQUENCE: 7

Gly Ser Gly Asp Ser Ala Thr His Ile Lys Phe Ser Lys Arg Asp Glu
1               5                   10                  15

Asp Gly Lys Glu Leu Ala Gly Ala Thr Met Glu Leu Arg Asp Ser Ser
            20                  25                  30

Gly Lys Thr Ile Ser Thr Trp Ile Ser Asp Gly Gln Val Lys Asp Phe
        35                  40                  45

Tyr Leu Tyr Pro Gly Lys Tyr Thr Phe Val Glu Thr Ala Ala Pro Asp
    50                  55                  60

Gly Tyr Glu Val Ala Thr Ala Ile Thr Phe Thr Val Asn Glu Gln Gly
65                  70                  75                  80

Gln Val Thr Val Asn Gly Lys Ala Thr Lys Gly Asp Ala His Ile Gly
            85                  90                  95

Val Asp

<210> SEQ ID NO 8
<211> LENGTH: 108
<212> TYPE: PRT
<213> ORGANISM: Artificial Sequence
<220> FEATURE:
<223> OTHER INFORMATION: Spycatcher Sequence with purification tag

<400> SEQUENCE: 8

Met Gly Ser Ser His His His His His His Gly Ser Gly Asp Ser Ala
1               5                   10                  15

Thr His Ile Lys Phe Ser Lys Arg Asp Glu Asp Gly Lys Glu Leu Ala
            20                  25                  30

Gly Ala Thr Met Glu Leu Arg Asp Ser Ser Gly Lys Thr Ile Ser Thr
        35                  40                  45

Trp Ile Ser Asp Gly Gln Val Lys Asp Phe Tyr Leu Tyr Pro Gly Lys
    50                  55                  60

Tyr Thr Phe Val Glu Thr Ala Ala Pro Asp Gly Tyr Glu Val Ala Thr
65                  70                  75                  80

Ala Ile Thr Phe Thr Val Asn Glu Gln Gly Gln Val Thr Val Asn Gly
            85                  90                  95

Lys Ala Thr Lys Gly Asp Ala His Ile Gly Val Asp
                100                 105

<210> SEQ ID NO 9
```

```
<211> LENGTH: 113
<212> TYPE: PRT
<213> ORGANISM: Artificial Sequence
<220> FEATURE:
<223> OTHER INFORMATION: SnoopCatcher Sequence

<400> SEQUENCE: 9

Met Lys Pro Leu Arg Gly Ala Val Phe Ser Leu Gln Lys Gln His Pro
1               5                   10                  15

Asp Tyr Pro Asp Ile Tyr Gly Ala Ile Asp Gln Asn Gly Thr Tyr Gln
            20                  25                  30

Asn Val Arg Thr Gly Glu Asp Gly Lys Leu Thr Phe Lys Asn Leu Ser
        35                  40                  45

Asp Gly Lys Tyr Arg Leu Phe Glu Asn Ser Glu Pro Ala Gly Tyr Lys
    50                  55                  60

Pro Val Gln Asn Lys Pro Ile Val Ala Phe Gln Ile Val Asn Gly Glu
65                  70                  75                  80

Val Arg Asp Val Thr Ser Ile Val Pro Gln Asp Ile Pro Ala Thr Tyr
                85                  90                  95

Glu Phe Thr Asn Gly Lys His Tyr Ile Thr Asn Glu Pro Ile Pro Pro
            100                 105                 110

Lys

<210> SEQ ID NO 10
<211> LENGTH: 5
<212> TYPE: PRT
<213> ORGANISM: Artificial Sequence
<220> FEATURE:
<223> OTHER INFORMATION: Synthetic sequence

<400> SEQUENCE: 10

Glu Ala Ala Ala Lys
1               5

<210> SEQ ID NO 11
<211> LENGTH: 333
<212> TYPE: PRT
<213> ORGANISM: Artificial Sequence
<220> FEATURE:
<223> OTHER INFORMATION: SpyCage(4xGGS)

<400> SEQUENCE: 11

Met Gly Ser Ser His His His His His His Gly Ser Gly Asp Ser Ala
1               5                   10                  15

Thr His Ile Lys Phe Ser Lys Arg Asp Glu Asp Gly Lys Glu Leu Ala
            20                  25                  30

Gly Ala Thr Met Glu Leu Arg Asp Ser Ser Gly Lys Thr Ile Ser Thr
        35                  40                  45

Trp Ile Ser Asp Gly Gln Val Lys Asp Phe Tyr Leu Tyr Pro Gly Lys
    50                  55                  60

Tyr Thr Phe Val Glu Thr Ala Ala Pro Asp Gly Tyr Glu Val Ala Thr
65                  70                  75                  80

Ala Ile Thr Phe Thr Val Asn Glu Gln Gly Gln Val Thr Val Asn Gly
                85                  90                  95

Lys Ala Thr Lys Gly Asp Ala His Ile Gly Val Asp His His His His
            100                 105                 110

His His Gly Gly Ser Gly Gly Ser Gly Gly Ser Gly Gly Ser Met Lys
        115                 120                 125

Met Glu Glu Leu Phe Lys Lys His Lys Ile Val Ala Val Leu Arg Ala
```

```
                    130                 135                 140
Asn Ser Val Glu Glu Ala Lys Lys Ala Leu Ala Val Phe Leu Gly
145                 150                 155                 160

Gly Val His Leu Ile Glu Ile Thr Phe Thr Val Pro Asp Ala Asp Thr
                    165                 170                 175

Val Ile Lys Glu Leu Ser Phe Leu Lys Glu Met Gly Ala Ile Ile Gly
                    180                 185                 190

Ala Gly Thr Val Thr Ser Val Glu Gln Cys Arg Lys Ala Val Glu Ser
                    195                 200                 205

Gly Ala Glu Phe Ile Val Ser Pro His Leu Asp Glu Glu Ile Ser Gln
                    210                 215                 220

Phe Cys Lys Glu Lys Gly Val Phe Tyr Met Pro Gly Val Met Thr Pro
225                 230                 235                 240

Thr Glu Leu Val Lys Ala Met Lys Leu Gly His Thr Ile Leu Lys Leu
                    245                 250                 255

Phe Pro Gly Glu Val Val Gly Pro Gln Phe Val Lys Ala Met Lys Gly
                    260                 265                 270

Pro Phe Pro Asn Val Lys Phe Val Pro Thr Gly Gly Val Asn Leu Asp
                    275                 280                 285

Asn Val Cys Glu Trp Phe Lys Ala Gly Val Leu Ala Val Gly Val Gly
                    290                 295                 300

Ser Ala Leu Val Lys Gly Thr Pro Val Glu Val Ala Glu Lys Ala Lys
305                 310                 315                 320

Ala Phe Val Glu Lys Ile Arg Gly Cys Thr Glu His Met
                    325                 330

<210> SEQ ID NO 12
<211> LENGTH: 340
<212> TYPE: PRT
<213> ORGANISM: Artificial Sequence
<220> FEATURE:
<223> OTHER INFORMATION: SpyCage(EAAAK-v1)

<400> SEQUENCE: 12

Met Gly Ser Ser His His His His His His Gly Ser Gly Asp Ser Ala
1               5                   10                  15

Thr His Ile Lys Phe Ser Lys Arg Asp Glu Asp Gly Lys Glu Leu Ala
                    20                  25                  30

Gly Ala Thr Met Glu Leu Arg Asp Ser Ser Gly Lys Thr Ile Ser Thr
                    35                  40                  45

Trp Ile Ser Asp Gly Gln Val Lys Asp Phe Tyr Leu Tyr Pro Gly Lys
                50                  55                  60

Tyr Thr Phe Val Glu Thr Ala Ala Pro Asp Gly Tyr Glu Val Ala Thr
65                  70                  75                  80

Ala Ile Thr Phe Thr Val Asn Glu Gln Gly Gln Val Thr Val Asn Gly
                    85                  90                  95

Lys Ala Thr Lys Gly Asp Ala His Ile Gly Val Asp Glu Ala Ala Ala
                    100                 105                 110

Lys Glu Ala Ala Ala Lys Glu Ala Ala Ala Lys Glu Ala Ala Ala Lys
                    115                 120                 125

Glu Ala Ala Ala Lys Ala Ser Met Glu Glu Leu Phe Lys Lys His Lys
                    130                 135                 140

Ile Val Ala Val Leu Arg Ala Asn Ser Val Glu Glu Ala Lys Lys Lys
145                 150                 155                 160

Ala Leu Ala Val Phe Leu Gly Gly Val His Leu Ile Glu Ile Thr Phe
```

```
                165                 170                 175
Thr Val Pro Asp Ala Asp Thr Val Ile Lys Glu Leu Ser Phe Leu Lys
            180                 185                 190

Glu Met Gly Ala Ile Ile Gly Ala Gly Thr Val Thr Ser Val Glu Gln
            195                 200                 205

Cys Arg Lys Ala Val Glu Ser Gly Ala Glu Phe Ile Val Ser Pro His
210                 215                 220

Leu Asp Glu Glu Ile Ser Gln Phe Cys Lys Lys Gly Val Phe Tyr
225                 230                 235                 240

Met Pro Gly Val Met Thr Pro Thr Glu Leu Val Lys Ala Met Lys Leu
            245                 250                 255

Gly His Thr Ile Leu Lys Leu Phe Pro Gly Glu Val Val Gly Pro Gln
            260                 265                 270

Phe Val Lys Ala Met Lys Gly Pro Phe Pro Asn Val Lys Phe Val Pro
            275                 280                 285

Thr Gly Gly Val Asn Leu Asp Asn Val Cys Glu Trp Phe Lys Ala Gly
            290                 295                 300

Val Leu Ala Val Gly Val Gly Ser Ala Leu Val Lys Gly Thr Pro Val
305                 310                 315                 320

Glu Val Ala Glu Lys Ala Lys Ala Phe Val Glu Lys Ile Arg Gly Cys
                325                 330                 335

Thr Glu His Met
            340

<210> SEQ ID NO 13
<211> LENGTH: 337
<212> TYPE: PRT
<213> ORGANISM: Artificial Sequence
<220> FEATURE:
<223> OTHER INFORMATION: SpyCage(EAAAK-v2)

<400> SEQUENCE: 13

Met Gly Ser Ser His His His His His His Gly Ser Gly Asp Ser Ala
1               5                   10                  15

Thr His Ile Lys Phe Ser Lys Arg Asp Glu Asp Gly Lys Glu Leu Ala
            20                  25                  30

Gly Ala Thr Met Glu Leu Arg Asp Ser Ser Gly Lys Thr Ile Ser Thr
        35                  40                  45

Trp Ile Ser Asp Gly Gln Val Lys Asp Phe Tyr Leu Tyr Pro Gly Lys
    50                  55                  60

Tyr Thr Phe Val Glu Thr Ala Ala Pro Asp Gly Tyr Glu Val Ala Thr
65                  70                  75                  80

Ala Ile Thr Phe Thr Val Asn Glu Gln Gly Gln Val Thr Val Asn Gly
                85                  90                  95

Lys Ala Thr Lys Gly Asp Ala His Ile Gly Val Asp Glu Ala Ala Ala
            100                 105                 110

Lys Glu Ala Ala Ala Lys Glu Ala Ala Ala Lys Glu Ala Ala Ala Lys
        115                 120                 125

Glu Ala Ala Ala Lys Glu Glu Leu Phe Lys Lys His Lys Ile Val Ala
    130                 135                 140

Val Leu Arg Ala Asn Ser Val Glu Glu Ala Lys Lys Ala Leu Ala
145                 150                 155                 160

Val Phe Leu Gly Gly Val His Leu Ile Glu Ile Thr Phe Thr Val Pro
                165                 170                 175

Asp Ala Asp Thr Val Ile Lys Glu Leu Ser Phe Leu Lys Glu Met Gly
```

```
                180                 185                 190
Ala Ile Ile Gly Ala Gly Thr Val Thr Ser Val Glu Gln Cys Arg Lys
            195                 200                 205

Ala Val Glu Ser Gly Ala Glu Phe Ile Val Ser Pro His Leu Asp Glu
        210                 215                 220

Glu Ile Ser Gln Phe Cys Lys Glu Lys Gly Val Phe Tyr Met Pro Gly
225                 230                 235                 240

Val Met Thr Pro Thr Glu Leu Val Lys Ala Met Lys Leu Gly His Thr
                245                 250                 255

Ile Leu Lys Leu Phe Pro Gly Glu Val Val Gly Pro Gln Phe Val Lys
            260                 265                 270

Ala Met Lys Gly Pro Phe Pro Asn Val Lys Phe Val Pro Thr Gly Gly
        275                 280                 285

Val Asn Leu Asp Asn Val Cys Glu Trp Phe Lys Ala Gly Val Leu Ala
            290                 295                 300

Val Gly Val Gly Ser Ala Leu Val Lys Gly Thr Pro Val Glu Val Ala
305                 310                 315                 320

Glu Lys Ala Lys Ala Phe Val Glu Lys Ile Arg Gly Cys Thr Glu His
                325                 330                 335

Met
```

```
<210> SEQ ID NO 14
<211> LENGTH: 321
<212> TYPE: PRT
<213> ORGANISM: Artificial Sequence
<220> FEATURE:
<223> OTHER INFORMATION: SpyCage(9xPro)

<400> SEQUENCE: 14
```

```
Met Gly Ser Ser His His His His His Gly Ser Gly Asp Ser Ala
1               5                   10                  15

Thr His Ile Lys Phe Ser Lys Arg Asp Glu Asp Gly Lys Glu Leu Ala
                20                  25                  30

Gly Ala Thr Met Glu Leu Arg Asp Ser Ser Gly Lys Thr Ile Ser Thr
            35                  40                  45

Trp Ile Ser Asp Gly Gln Val Lys Asp Phe Tyr Leu Tyr Pro Gly Lys
        50                  55                  60

Tyr Thr Phe Val Glu Thr Ala Ala Pro Asp Gly Tyr Glu Val Ala Thr
65                  70                  75                  80

Ala Ile Thr Phe Thr Val Asn Glu Gln Gly Gln Val Thr Val Asn Gly
                85                  90                  95

Lys Ala Thr Lys Gly Asp Ala His Ile Gly Val Asp Pro Pro Pro Pro
            100                 105                 110

Pro Pro Pro Pro Pro Glu Glu Leu Phe Lys Lys His Lys Ile Val Ala
        115                 120                 125

Val Leu Arg Ala Asn Ser Val Glu Glu Ala Lys Lys Lys Ala Leu Ala
130                 135                 140

Val Phe Leu Gly Gly Val His Leu Ile Glu Ile Thr Phe Thr Val Pro
145                 150                 155                 160

Asp Ala Asp Thr Val Ile Lys Glu Leu Ser Phe Leu Lys Glu Met Gly
                165                 170                 175

Ala Ile Ile Gly Ala Gly Thr Val Thr Ser Val Glu Gln Cys Arg Lys
            180                 185                 190

Ala Val Glu Ser Gly Ala Glu Phe Ile Val Ser Pro His Leu Asp Glu
        195                 200                 205
```

```
Glu Ile Ser Gln Phe Cys Lys Glu Lys Gly Val Phe Tyr Met Pro Gly
    210                 215                 220
Val Met Thr Pro Thr Glu Leu Val Lys Ala Met Lys Leu Gly His Thr
225                 230                 235                 240
Ile Leu Lys Leu Phe Pro Gly Glu Val Gly Pro Gln Phe Val Lys
                    245                 250                 255
Ala Met Lys Gly Pro Phe Pro Asn Val Lys Phe Val Pro Thr Gly Gly
                260                 265                 270
Val Asn Leu Asp Asn Val Cys Glu Trp Phe Lys Ala Gly Val Leu Ala
                275                 280                 285
Val Gly Val Gly Ser Ala Leu Val Lys Gly Thr Pro Val Glu Val Ala
    290                 295                 300
Glu Lys Ala Lys Ala Phe Val Glu Lys Ile Arg Gly Cys Thr Glu His
305                 310                 315                 320
Met
```

<210> SEQ ID NO 15
<211> LENGTH: 321
<212> TYPE: PRT
<213> ORGANISM: Artificial Sequence
<220> FEATURE:
<223> OTHER INFORMATION: SpyCage(3xPPA)

<400> SEQUENCE: 15

```
Met Gly Ser Ser His His His His His His Gly Ser Gly Asp Ser Ala
1               5                   10                  15
Thr His Ile Lys Phe Ser Lys Arg Asp Glu Asp Gly Lys Glu Leu Ala
                20                  25                  30
Gly Ala Thr Met Glu Leu Arg Asp Ser Ser Gly Lys Thr Ile Ser Thr
                35                  40                  45
Trp Ile Ser Asp Gly Gln Val Lys Asp Phe Tyr Leu Tyr Pro Gly Lys
    50                  55                  60
Tyr Thr Phe Val Glu Thr Ala Ala Pro Asp Gly Tyr Glu Val Ala Thr
65                  70                  75                  80
Ala Ile Thr Phe Thr Val Asn Glu Gln Gly Gln Val Thr Val Asn Gly
                85                  90                  95
Lys Ala Thr Lys Gly Asp Ala His Ile Gly Val Asp Pro Ala Pro
                100                 105                 110
Pro Ala Pro Pro Ala Glu Glu Leu Phe Lys Lys His Lys Ile Val Ala
            115                 120                 125
Val Leu Arg Ala Asn Ser Val Glu Ala Lys Lys Lys Ala Leu Ala
    130                 135                 140
Val Phe Leu Gly Gly Val His Leu Ile Glu Ile Thr Phe Thr Val Pro
145                 150                 155                 160
Asp Ala Asp Thr Val Ile Lys Glu Leu Ser Phe Leu Lys Glu Met Gly
                165                 170                 175
Ala Ile Ile Gly Ala Gly Thr Val Thr Ser Val Glu Gln Cys Arg Lys
                180                 185                 190
Ala Val Glu Ser Gly Ala Glu Phe Ile Val Ser Pro His Leu Asp Glu
            195                 200                 205
Glu Ile Ser Gln Phe Cys Lys Glu Lys Gly Val Phe Tyr Met Pro Gly
    210                 215                 220
Val Met Thr Pro Thr Glu Leu Val Lys Ala Met Lys Leu Gly His Thr
225                 230                 235                 240
```

```
Ile Leu Lys Leu Phe Pro Gly Glu Val Val Gly Pro Gln Phe Val Lys
                245                 250                 255

Ala Met Lys Gly Pro Phe Pro Asn Val Lys Phe Val Pro Thr Gly Gly
            260                 265                 270

Val Asn Leu Asp Asn Val Cys Glu Trp Phe Lys Ala Gly Val Leu Ala
        275                 280                 285

Val Gly Val Gly Ser Ala Leu Val Lys Gly Thr Pro Val Glu Val Ala
    290                 295                 300

Glu Lys Ala Lys Ala Phe Val Glu Lys Ile Arg Gly Cys Thr Glu His
305                 310                 315                 320

Met

<210> SEQ ID NO 16
<211> LENGTH: 1072
<212> TYPE: PRT
<213> ORGANISM: Artificial Sequence
<220> FEATURE:
<223> OTHER INFORMATION: cytosolic Poly-A Binding Protein (PABP)

<400> SEQUENCE: 16

Met Thr Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
            20                  25                  30

His Leu Tyr Glu Arg Asp Glu Gly Asp Lys Trp Arg Asn Lys Lys Phe
        35                  40                  45

Glu Leu Gly Leu Glu Phe Pro Asn Leu Pro Tyr Tyr Ile Asp Gly Asp
    50                  55                  60

Val Lys Leu Thr Gln Ser Met Ala Ile Ile Arg Tyr Ile Ala Asp Lys
65                  70                  75                  80

His Asn Met Leu Gly Gly Cys Pro Lys Glu Arg Ala Glu Ile Ser Met
                85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Ile Ala Trp Pro Leu Gln Gly Trp
        195                 200                 205

Gln Ala Thr Phe Gly Gly Gly Asp His Pro Pro Lys Ser Asp Leu Val
    210                 215                 220

Pro Arg Gly Ser Ser Met Gly Met Ile Ala Asn Ser Thr Asn Ile Met
225                 230                 235                 240

Pro Pro Ser Phe Ser Thr Ala Ser Leu Tyr Val Gly Asp Leu Ser Glu
                245                 250                 255

Asp Val Thr Glu Ala Val Leu Tyr Glu Ile Phe Asn Thr Val Gly His
            260                 265                 270

Val Leu Ser Ile Arg Val Cys Arg Asp Ser Val Thr Arg Lys Ser Leu
```

```
                275                 280                 285
Gly Tyr Ala Tyr Val Asn Tyr His Asn Leu Ala Asp Ala Glu Arg Ala
290                 295                 300

Leu Asp Thr Leu Asn Tyr Thr Asn Ile Lys Gly Gln Pro Ala Arg Leu
305                 310                 315                 320

Met Trp Ser His Arg Asp Pro Ser Leu Arg Lys Ser Gly Thr Gly Asn
                325                 330                 335

Ile Phe Val Lys Asn Leu Asp Lys Thr Ile Asp Asn Lys Ala Leu Phe
                340                 345                 350

Asp Thr Phe Ser Met Phe Gly Asn Ile Leu Ser Cys Lys Val Ala Thr
                355                 360                 365

Asp Glu Phe Gly Lys Ser Lys Asn Tyr Gly Phe Val His Tyr Glu Asp
                370                 375                 380

Glu Glu Ser Ala Lys Glu Ala Ile Glu Lys Val Asn Gly Met Gln Leu
385                 390                 395                 400

Gly Ser Lys Asn Val Tyr Val Gly His Phe Ile Lys Lys Ser Glu Arg
                405                 410                 415

Ala Thr Asn Asp Thr Lys Phe Thr Asn Leu Tyr Val Lys Asn Phe Pro
                420                 425                 430

Asp Thr Val Thr Glu Ala His Leu Lys Gln Leu Phe Ser Pro Tyr Gly
                435                 440                 445

Glu Ile Thr Ser Met Ile Val Lys Ser Asp Asn Lys Asn Arg Lys Phe
450                 455                 460

Cys Phe Ile Asn Tyr Ser Asp Ala Asp Ser Ala Arg Asn Ala Met Glu
465                 470                 475                 480

Asn Leu Asn Gly Lys Lys Ile Thr Glu Asp Gly Lys Ile Asp Tyr Asn
                485                 490                 495

Tyr Asp Pro Lys Lys Glu Glu Thr Glu Lys Pro Ala Asn Glu Asn Ser
                500                 505                 510

Asn Asn Asn Thr Thr Thr Glu Glu Asn Thr Thr Ser Glu Thr Pro
                515                 520                 525

Ala Glu Lys Lys Thr Pro Asp Ser Glu Pro Ala Thr Asn Lys Asp Ala
                530                 535                 540

Thr Pro Gly Glu Asp Gln Thr Ser Ala Asn Gly Thr Thr Thr Thr Val
545                 550                 555                 560

Thr Ser Thr Thr Asp Ala Asn Pro Asp Ser Lys Thr Glu Glu Thr Pro
                565                 570                 575

Asn Asp Asn Thr Ala Asn Ala Gly Thr Asn Ala Ser Thr Thr Glu Lys
                580                 585                 590

Lys Asp Asn Lys Lys Ser Gly Glu Asn Thr Glu Thr Pro Asn Ile Leu
                595                 600                 605

Tyr Val Gly Pro His Gln Ser Arg Ala Arg Arg His Ala Ile Leu Lys
                610                 615                 620

Ala Lys Phe Asp Thr Leu Asn Thr Glu Ser Arg Asn Lys His Pro Gly
625                 630                 635                 640

Val Asn Leu Tyr Ile Lys Asn Leu Asp Asp Ser Met Asn Asp Gln Thr
                645                 650                 655

Leu Lys Glu Leu Phe Glu Pro Tyr Gly Thr Ile Thr Ser Ala Lys Val
                660                 665                 670

Met Lys Asp Asp Lys Asp Gln Ser Lys Gly Phe Gly Phe Val Cys Phe
                675                 680                 685

Gly Thr His Glu Glu Ala Asn Lys Ala Val Thr Glu Met His Leu Lys
                690                 695                 700
```

-continued

```
Ile Ile Asn Gly Lys Pro Leu Tyr Val Gly Leu Ala Glu Lys Arg Glu
705                 710                 715                 720

Gln Arg Leu Ser Arg Leu Gln Gln Arg Phe Arg Met His Pro Ile Arg
            725                 730                 735

His His Ile Asn Asn Ala Leu Asn Ala Pro Ile Gln Tyr Pro Asn Ser
        740                 745                 750

Gln Thr Ala Gln Leu Gln Phe Asn Gln Asn Thr Leu Asn Tyr Gly Arg
    755                 760                 765

Pro Val Ile Thr Ser Phe Asn Gln Asn Asn Leu Ile Ser Trp Arg His
770                 775                 780

Gln Gln Ala Ala Ala Gln Gln Ala Ala His Gln Gln Ala Ala
785                 790                 795                 800

Gln Gln Gln Leu Gly Phe Asn Gly Gly Leu Arg Gly Gln Ile Asn Gln
                805                 810                 815

Met Arg Leu Tyr Thr Gln Asn Asn Met Ile Asn His Asn Ile Gly Gln
                820                 825                 830

Asn Lys Ala Asn Gln Gln Leu His His Asn Gln Gln Tyr Pro Ile Gly
            835                 840                 845

Pro Asn Pro Gln His Gln Gln Thr Asn Leu Asn Ala Pro Ala Gln Thr
        850                 855                 860

Asn Pro Gln Gln Leu Gln Gly Ala Ala Pro Val Pro Thr Asn Gln Leu
865                 870                 875                 880

Leu Asn Asn Asn Met Arg Asn Met Asn Ser Arg Gly Asn Arg Asn Leu
                885                 890                 895

Pro Gly Ile Asn Ile Gln Ser Pro Lys Gln Met Pro Leu Asn Met Val
                900                 905                 910

Gly Ala Lys Gln Thr Asn Pro Gln Gln Asn Gln Pro Gln Asn Gln Pro
            915                 920                 925

Gln Asn Gln Pro Gln Gly Gln Pro Gln Asn Gln Pro Gln Gln Lys Ser
        930                 935                 940

Gly Gln Ser Ile Gln Gln Gln Gln Gln Gln Gln Gln Gln Gln Thr Ile
945                 950                 955                 960

Pro Gln Asn Asn Asn Phe Lys Phe Thr Ser Gln Ala Arg Asn Arg Met
                965                 970                 975

Glu Leu Pro Asn Lys Asn Gly Asn Lys Val Asn Asn Met Thr Pro Gly
            980                 985                 990

Tyr Asn Asn Asn Thr Thr Leu Thr Ala Ala Ala Leu Ala Ser Ala Pro
        995                 1000                1005

Pro Ser Met Gln Lys Gln Val Leu Gly Glu Asn Leu Phe Pro Leu
    1010                1015                1020

Val Ala Asn Tyr His Pro Thr Leu Ala Gly Lys Ile Thr Gly Met
    1025                1030                1035

Met Leu Glu Met Asp Asn Ser Glu Leu Leu Ile Leu Leu Glu Asn
    1040                1045                1050

Glu Asp Gln Leu Lys Lys Lys Ile Asp Glu Ala Leu Ala Val Leu
    1055                1060                1065

Gln Asn Ala Lys
    1070
```

<210> SEQ ID NO 17
<211> LENGTH: 135
<212> TYPE: PRT
<213> ORGANISM: Artificial Sequence
<220> FEATURE:

<223> OTHER INFORMATION: DNA-binding protein of the ApiAP2 specific transcription factor family

<400> SEQUENCE: 17

Gly Ser Gln Glu Pro Val Ile Leu Ile Asp Lys Ile Glu Arg Cys Leu
1               5                   10                  15

Val Val Glu Trp Tyr Glu Asn Asn Ile Arg Arg Glu Gln Arg Ile Ser
            20                  25                  30

Tyr Lys Lys Tyr Gly Asn Asp Lys Ala Lys Leu Arg Ala Lys Glu Leu
        35                  40                  45

Ile Glu Lys Leu Lys Ser Gly Ile Thr Phe Glu Gln Leu Tyr Pro Asp
    50                  55                  60

Lys Gly Pro Pro Ile Val Arg Val Phe Glu Asn Val Gly Val Tyr Asn
65                  70                  75                  80

Val Ser Leu Ile Arg Asp Arg Ile Glu Arg Glu Trp Arg Val Glu Trp
                85                  90                  95

Leu Glu Asn Gly Val Pro Met Lys Ala Arg Trp Ser Cys Lys Lys Val
            100                 105                 110

Gly Asn Asp Glu Ala Gln Lys Arg Ala Asp Thr Phe Ala Gln Ser Met
        115                 120                 125

Ile Lys Gly Ile Phe Asn Pro
    130                 135

<210> SEQ ID NO 18
<211> LENGTH: 198
<212> TYPE: PRT
<213> ORGANISM: Artificial Sequence
<220> FEATURE:
<223> OTHER INFORMATION: binding domain of tristetraprolin (TTP) of a NOT family protein

<400> SEQUENCE: 18

Asn Asn Asn Phe Asn Ile Asn Leu Gln Ile Glu Asp Gly Ile Thr Asn
1               5                   10                  15

Lys Tyr Glu Ala Glu Val Asn Gly Tyr Phe Ala Lys Leu Tyr Thr Gly
            20                  25                  30

Glu Ile Thr Val Asn Thr Met Ile Asp Ile Met Lys Asn Leu Ser Cys
        35                  40                  45

Ser Pro Lys Gly Ser Lys Asn Asn Asp Ile Tyr Lys Ser Met Leu Leu
    50                  55                  60

Ile Leu Phe Asn Glu Cys Lys Phe Phe Pro Lys Tyr Pro Val Glu Glu
65                  70                  75                  80

Leu Asp Ile Thr Ala Gln Leu Phe Gly Lys Leu Ile Lys His Asn Leu
                85                  90                  95

Leu Ile Ser Tyr Gly Asn Thr Leu Ser Val Val Leu Lys Cys Ile Leu
            100                 105                 110

Glu Ala Leu Lys Lys Gly Ser Asp Ser Lys Val Phe Asn Phe Gly Ile
        115                 120                 125

Thr Ala Leu Glu Gln Phe Glu Asp Ser Leu Ile Cys Tyr Pro Ala Phe
    130                 135                 140

Leu Ser Ser Leu Ile Pro Leu Pro Thr Leu Arg Gln Tyr Asn Pro Gln
145                 150                 155                 160

Tyr Ile Ile His Cys Asn Glu Leu Leu Asn Thr Leu Pro Glu Gln Phe
                165                 170                 175

Arg Thr Leu Pro Tyr Ile Asp Ala Ser Thr Ile Leu Lys Ile Lys His
            180                 185                 190

Ile Ser Glu Ile Ser Ser
        195

<210> SEQ ID NO 19
<211> LENGTH: 194
<212> TYPE: PRT
<213> ORGANISM: Artificial Sequence
<220> FEATURE:
<223> OTHER INFORMATION: RNA-recognition motif of the Upregulated in
      Infectious Sporozoites 12 (UIS12) protein

<400> SEQUENCE: 19

Lys Asn Val Ile Ile Thr Asn Val Phe Leu Gly Asn Ile Pro Pro Asn
1               5                   10                  15

Ile Thr Glu Glu Arg Leu Lys Asn Val Leu Glu Ile Phe Gly Tyr Ile
            20                  25                  30

Ile His Ile Glu Tyr Lys Trp Ser Leu Asp Lys Trp Ser Tyr Ala Phe
        35                  40                  45

Ile Tyr Phe Ile Glu Glu Lys Cys Ala Ile Asn Ala Val Asn Ile Leu
    50                  55                  60

Asn Gln Lys Lys Phe Phe Asp Asn Ser Pro Asn His Lys Leu Ile Cys
65                  70                  75                  80

Phe Ile Val Ser Lys Gln Ile Pro Asn Gln Asn Thr Leu His Tyr Ser
                85                  90                  95

Lys Ala Asn Phe Ser Leu Leu Lys Asp Gly Pro Pro Gly Ala Asn Leu
            100                 105                 110

Phe Leu Tyr Gly Ile Pro Leu Lys Trp Thr Glu Leu Asn Leu Ile Gln
        115                 120                 125

Leu Val Asn Lys Tyr Gly His Val Val Gly Leu Arg Ile Pro Tyr Ile
    130                 135                 140

Asn Asn Asp Asn Asp Lys Lys Gln Gly Asn Arg Gly Phe Gly Phe Val
145                 150                 155                 160

Ser Tyr Asp Asn Lys Lys Ser Ala Val Glu Ala Phe Glu Glu Leu Ser
                165                 170                 175

Lys Met Tyr Ile His Gly Lys Leu Leu Lys Val Gln Leu Lys Asn Gly
            180                 185                 190

Glu Glu

<210> SEQ ID NO 20
<211> LENGTH: 13
<212> TYPE: PRT
<213> ORGANISM: Artificial Sequence
<220> FEATURE:
<223> OTHER INFORMATION: Spytag sequence

<400> SEQUENCE: 20

Ala His Ile Val Met Val Asp Ala Tyr Lys Pro Thr Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: SnoopTag

<400> SEQUENCE: 21

Lys Leu Gly Asp Ile Glu Phe Ile Lys Val Asn Lys Gly
1               5                   10

<210> SEQ ID NO 22
<211> LENGTH: 1103
<212> TYPE: PRT
<213> ORGANISM: Artificial Sequence
<220> FEATURE:
<223> OTHER INFORMATION: PyPABP1-SpyTag

<400> SEQUENCE: 22

```
Met Thr Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
            20                  25                  30

His Leu Tyr Glu Arg Asp Glu Gly Asp Lys Trp Arg Asn Lys Lys Phe
        35                  40                  45

Glu Leu Gly Leu Glu Phe Pro Asn Leu Pro Tyr Tyr Ile Asp Gly Asp
    50                  55                  60

Val Lys Leu Thr Gln Ser Met Ala Ile Ile Arg Tyr Ile Ala Asp Lys
65                  70                  75                  80

His Asn Met Leu Gly Gly Cys Pro Lys Glu Arg Ala Glu Ile Ser Met
                85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Ile Ala Trp Pro Leu Gln Gly Trp
        195                 200                 205

Gln Ala Thr Phe Gly Gly Gly Asp His Pro Pro Lys Ser Asp Leu Val
    210                 215                 220

Pro Arg Gly Ser Ser Met Gly Met Ile Ala Asn Ser Thr Asn Ile Met
225                 230                 235                 240

Pro Pro Ser Phe Ser Thr Ala Ser Leu Tyr Val Gly Asp Leu Ser Glu
                245                 250                 255

Asp Val Thr Glu Ala Val Leu Tyr Glu Ile Phe Asn Thr Val Gly His
            260                 265                 270

Val Leu Ser Ile Arg Val Cys Arg Asp Ser Val Thr Arg Lys Ser Leu
        275                 280                 285

Gly Tyr Ala Tyr Val Asn Tyr His Asn Leu Ala Asp Ala Glu Arg Ala
    290                 295                 300

Leu Asp Thr Leu Asn Tyr Thr Asn Ile Lys Gly Gln Pro Ala Arg Leu
305                 310                 315                 320

Met Trp Ser His Arg Asp Pro Ser Leu Arg Lys Ser Gly Thr Gly Asn
                325                 330                 335

Ile Phe Val Lys Asn Leu Asp Lys Thr Ile Asp Asn Lys Ala Leu Phe
            340                 345                 350

Asp Thr Phe Ser Met Phe Gly Asn Ile Leu Ser Cys Lys Val Ala Thr
        355                 360                 365

Asp Glu Phe Gly Lys Ser Lys Asn Tyr Gly Phe Val His Tyr Glu Asp
```

```
                370                 375                 380
Glu Glu Ser Ala Lys Glu Ala Ile Glu Lys Val Asn Gly Met Gln Leu
385                 390                 395                 400

Gly Ser Lys Asn Val Tyr Val Gly His Phe Ile Lys Lys Ser Glu Arg
                405                 410                 415

Ala Thr Asn Asp Thr Lys Phe Thr Asn Leu Tyr Val Lys Asn Phe Pro
                420                 425                 430

Asp Thr Val Thr Glu Ala His Leu Lys Gln Leu Phe Ser Pro Tyr Gly
                435                 440                 445

Glu Ile Thr Ser Met Ile Val Lys Ser Asp Asn Lys Asn Arg Lys Phe
            450                 455                 460

Cys Phe Ile Asn Tyr Ser Asp Ala Asp Ser Ala Arg Asn Ala Met Glu
465                 470                 475                 480

Asn Leu Asn Gly Lys Lys Ile Thr Glu Asp Gly Lys Ile Asp Tyr Asn
                485                 490                 495

Tyr Asp Pro Lys Lys Glu Glu Thr Glu Lys Pro Ala Asn Glu Asn Ser
                500                 505                 510

Asn Asn Asn Thr Thr Thr Glu Glu Asn Thr Thr Ser Glu Thr Pro
            515                 520                 525

Ala Glu Lys Lys Thr Pro Asp Ser Glu Pro Ala Thr Asn Lys Asp Ala
530                 535                 540

Thr Pro Gly Glu Asp Gln Thr Ser Ala Asn Gly Thr Thr Thr Val
545                 550                 555                 560

Thr Ser Thr Thr Asp Ala Asn Pro Asp Ser Lys Thr Glu Glu Thr Pro
                565                 570                 575

Asn Asp Asn Thr Ala Asn Ala Gly Thr Asn Ala Ser Thr Thr Glu Lys
                580                 585                 590

Lys Asp Asn Lys Lys Ser Gly Glu Asn Thr Glu Thr Pro Asn Ile Leu
                595                 600                 605

Tyr Val Gly Pro His Gln Ser Arg Ala Arg His Ala Ile Leu Lys
            610                 615                 620

Ala Lys Phe Asp Thr Leu Asn Thr Glu Ser Arg Asn Lys His Pro Gly
625                 630                 635                 640

Val Asn Leu Tyr Ile Lys Asn Leu Asp Asp Ser Met Asn Asp Gln Thr
                645                 650                 655

Leu Lys Glu Leu Phe Glu Pro Tyr Gly Thr Ile Thr Ser Ala Lys Val
                660                 665                 670

Met Lys Asp Asp Lys Asp Gln Ser Lys Gly Phe Gly Phe Val Cys Phe
                675                 680                 685

Gly Thr His Glu Glu Ala Asn Lys Ala Val Thr Glu Met His Leu Lys
            690                 695                 700

Ile Ile Asn Gly Lys Pro Leu Tyr Val Gly Leu Ala Glu Lys Arg Glu
705                 710                 715                 720

Gln Arg Leu Ser Arg Leu Gln Gln Arg Phe Arg Met His Pro Ile Arg
                725                 730                 735

His His Ile Asn Asn Ala Leu Asn Ala Pro Ile Gln Tyr Pro Asn Ser
                740                 745                 750

Gln Thr Ala Gln Leu Gln Phe Asn Gln Asn Thr Leu Asn Tyr Gly Arg
                755                 760                 765

Pro Val Ile Thr Ser Phe Asn Gln Asn Asn Leu Ile Ser Trp Arg His
                770                 775                 780

Gln Gln Ala Ala Ala Gln Gln Ala Ala His Gln Gln Ala Ala Ala
785                 790                 795                 800
```

-continued

```
Gln Gln Gln Leu Gly Phe Asn Gly Gly Leu Arg Gly Gln Ile Asn Gln
                805                 810                 815

Met Arg Leu Tyr Thr Gln Asn Asn Met Ile Asn His Asn Ile Gly Gln
            820                 825                 830

Asn Lys Ala Asn Gln Gln Leu His His Asn Gln Gln Tyr Pro Ile Gly
        835                 840                 845

Pro Asn Pro Gln His Gln Gln Thr Asn Leu Asn Ala Pro Ala Gln Thr
    850                 855                 860

Asn Pro Gln Gln Leu Gln Gly Ala Ala Pro Val Pro Thr Asn Gln Leu
865                 870                 875                 880

Leu Asn Asn Asn Met Arg Asn Met Asn Ser Arg Gly Asn Arg Asn Leu
                885                 890                 895

Pro Gly Ile Asn Ile Gln Ser Pro Lys Gln Met Pro Leu Asn Met Val
            900                 905                 910

Gly Ala Lys Gln Thr Asn Pro Gln Gln Asn Gln Pro Gln Asn Gln Pro
        915                 920                 925

Gln Asn Gln Pro Gln Gly Gln Pro Gln Asn Gln Pro Gln Gln Lys Ser
    930                 935                 940

Gly Gln Ser Ile Gln Gln Gln Gln Gln Gln Gln Gln Gln Gln Thr Ile
945                 950                 955                 960

Pro Gln Asn Asn Asn Phe Lys Phe Thr Ser Gln Ala Arg Asn Arg Met
                965                 970                 975

Glu Leu Pro Asn Lys Asn Gly Asn Lys Val Asn Asn Met Thr Pro Gly
            980                 985                 990

Tyr Asn Asn Asn Thr Thr Leu Thr Ala Ala Ala Leu Ala Ser Ala Pro
        995                 1000                1005

Pro Ser Met Gln Lys Gln Val Leu Gly Glu Asn Leu Phe Pro Leu
    1010                1015                1020

Val Ala Asn Tyr His Pro Thr Leu Ala Gly Lys Ile Thr Gly Met
    1025                1030                1035

Met Leu Glu Met Asp Asn Ser Glu Leu Ile Leu Leu Glu Asn
    1040                1045                1050

Glu Asp Gln Leu Lys Lys Lys Ile Asp Glu Ala Leu Ala Val Leu
    1055                1060                1065

Gln Asn Ala Lys Leu Glu Ala His Ile Val Met Val Asp Ala Tyr
    1070                1075                1080

Lys Pro Thr Lys Val Glu Asn Leu Tyr Phe Gln Gly Val Glu His
    1085                1090                1095

His His His His
    1100

<210> SEQ ID NO 23
<211> LENGTH: 379
<212> TYPE: PRT
<213> ORGANISM: Artificial Sequence
<220> FEATURE:
<223> OTHER INFORMATION: SpyTag-2xAP2

<400> SEQUENCE: 23

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45
```

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser His Ser Ala His Ile Val Met Val Asp Ala Tyr Lys Pro Thr
225                 230                 235                 240

Lys Ala Met Ile Gly Ser Gln Glu Pro Val Ile Leu Ile Asp Lys Ile
                245                 250                 255

Glu Arg Cys Leu Val Val Glu Trp Tyr Glu Asn Asn Ile Arg Arg Glu
            260                 265                 270

Gln Arg Ile Ser Tyr Lys Lys Tyr Gly Asn Asp Lys Ala Lys Leu Arg
        275                 280                 285

Ala Lys Glu Leu Ile Glu Lys Leu Lys Ser Gly Ile Thr Phe Glu Gln
    290                 295                 300

Leu Tyr Pro Asp Lys Gly Pro Pro Ile Val Arg Val Phe Glu Asn Val
305                 310                 315                 320

Gly Val Tyr Asn Val Ser Leu Ile Arg Asp Arg Ile Glu Arg Glu Trp
                325                 330                 335

Arg Val Glu Trp Leu Glu Asn Gly Val Pro Met Lys Ala Arg Trp Ser
            340                 345                 350

Cys Lys Lys Val Gly Asn Asp Glu Ala Gln Lys Arg Ala Asp Thr Phe
        355                 360                 365

Ala Gln Ser Met Ile Lys Gly Ile Phe Asn Pro
    370                 375

<210> SEQ ID NO 24
<211> LENGTH: 463
<212> TYPE: PRT
<213> ORGANISM: Artificial Sequence
<220> FEATURE:
<223> OTHER INFORMATION: SpyTag-TTP BD

<400> SEQUENCE: 24

Met Thr Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
            20                  25                  30

```
His Leu Tyr Glu Arg Asp Gly Asp Lys Trp Arg Asn Lys Lys Phe
        35                  40                  45

Glu Leu Gly Leu Glu Phe Pro Asn Leu Pro Tyr Tyr Ile Asp Gly Asp
 50                  55                  60

Val Lys Leu Thr Gln Ser Met Ala Ile Ile Arg Tyr Ile Ala Asp Lys
 65                  70                  75                  80

His Asn Met Leu Gly Gly Cys Pro Lys Glu Arg Ala Glu Ile Ser Met
                    85                  90                  95

Leu Glu Gly Ala Val Leu Asp Ile Arg Tyr Gly Val Ser Arg Ile Ala
                100                 105                 110

Tyr Ser Lys Asp Phe Glu Thr Leu Lys Val Asp Phe Leu Ser Lys Leu
                115                 120                 125

Pro Glu Met Leu Lys Met Phe Glu Asp Arg Leu Cys His Lys Thr Tyr
            130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                    165                 170                 175

Lys Leu Val Cys Phe Lys Lys Arg Ile Glu Ala Ile Pro Gln Ile Asp
                180                 185                 190

Lys Tyr Leu Lys Ser Ser Lys Tyr Ile Ala Trp Pro Leu Gln Gly Trp
                195                 200                 205

Gln Ala Thr Phe Gly Gly Gly Asp His Pro Pro Lys Ser Asp Leu Val
            210                 215                 220

Pro Arg Gly Ser Ser Met Gly Ser Ser His His His His His His Ser
225                 230                 235                 240

Ser Gly Leu Val Pro Arg Gly Ser His Ile Ala His Ile Val Met Val
                    245                 250                 255

Asp Ala Tyr Lys Pro Thr Lys His Met Asn Asn Asn Phe Asn Ile Asn
                260                 265                 270

Leu Gln Ile Glu Asp Gly Ile Thr Asn Lys Tyr Glu Ala Glu Val Asn
            275                 280                 285

Gly Tyr Phe Ala Lys Leu Tyr Thr Gly Glu Ile Thr Val Asn Thr Met
290                 295                 300

Ile Asp Ile Met Lys Asn Leu Ser Cys Ser Pro Lys Gly Ser Lys Asn
305                 310                 315                 320

Asn Asp Ile Tyr Lys Ser Met Leu Leu Ile Leu Phe Asn Glu Cys Lys
                325                 330                 335

Phe Phe Pro Lys Tyr Pro Val Glu Glu Leu Asp Ile Thr Ala Gln Leu
                340                 345                 350

Phe Gly Lys Leu Ile Lys His Asn Leu Leu Ile Ser Tyr Gly Asn Thr
            355                 360                 365

Leu Ser Val Val Leu Lys Cys Ile Leu Glu Ala Leu Lys Lys Gly Ser
370                 375                 380

Asp Ser Lys Val Phe Asn Phe Gly Ile Thr Ala Leu Glu Gln Phe Glu
385                 390                 395                 400

Asp Ser Leu Ile Cys Tyr Pro Ala Phe Leu Ser Ser Leu Ile Pro Leu
                405                 410                 415

Pro Thr Leu Arg Gln Tyr Asn Pro Gln Tyr Ile Ile His Cys Asn Glu
            420                 425                 430

Leu Leu Asn Thr Leu Pro Glu Gln Phe Arg Thr Leu Pro Tyr Ile Asp
            435                 440                 445
```

Ala Ser Thr Ile Leu Lys Ile Lys His Ile Ser Glu Ile Ser Ser
    450                 455                 460

<210> SEQ ID NO 25
<211> LENGTH: 475
<212> TYPE: PRT
<213> ORGANISM: Artificial Sequence
<220> FEATURE:
<223> OTHER INFORMATION: SpyTag-UIS12 RRM 1+2

<400> SEQUENCE: 25

Met Thr Met Ser Pro Ile Leu Gly Tyr Trp Lys Ile Lys Gly Leu Val
1               5                   10                  15

Gln Pro Thr Arg Leu Leu Leu Glu Tyr Leu Glu Glu Lys Tyr Glu Glu
            20                  25                  30

His Leu Tyr Glu Arg Asp Glu Gly Asp Lys Trp Arg Asn Lys Lys Phe
        35                  40                  45

Glu Leu Gly Leu Glu Phe Pro Asn Leu Pro Tyr Tyr Ile Asp Gly Asp
    50                  55                  60

Val Lys Leu Thr Gln Ser Met Ala Ile Ile Arg Tyr Ile Ala Asp Lys
65                  70                  75                  80

His Asn Met Leu Gly Gly Cys Pro Lys Glu Arg Ala Glu Ile Ser Met
                85                  90                  95

Leu Glu Gly Ala Val Leu Asp Ile Arg Tyr Gly Val Ser Arg Ile Ala
            100                 105                 110

Tyr Ser Lys Asp Phe Glu Thr Leu Lys Val Asp Phe Leu Ser Lys Leu
        115                 120                 125

Pro Glu Met Leu Lys Met Phe Glu Asp Arg Leu Cys His Lys Thr Tyr
    130                 135                 140

Leu Asn Gly Asp His Val Thr His Pro Asp Phe Met Leu Tyr Asp Ala
145                 150                 155                 160

Leu Asp Val Val Leu Tyr Met Asp Pro Met Cys Leu Asp Ala Phe Pro
                165                 170                 175

Lys Leu Val Cys Phe Lys Lys Arg Ile Glu Ala Ile Pro Gln Ile Asp
            180                 185                 190

Lys Tyr Leu Lys Ser Ser Lys Tyr Ile Ala Trp Pro Leu Gln Gly Trp
        195                 200                 205

Gln Ala Thr Phe Gly Gly Gly Asp His Pro Pro Lys Ser Asp Leu Val
    210                 215                 220

Pro Arg Gly Ser Ser Met Gly Ser Ser His His His His His His Ser
225                 230                 235                 240

Ser Gly Leu Val Pro Arg Gly Ser His Ile Ala His Ile Val Met Val
                245                 250                 255

Asp Ala Tyr Lys Pro Thr Lys His Met Lys Asn Val Ile Ile Thr Asn
            260                 265                 270

Val Phe Leu Gly Asn Ile Pro Pro Asn Ile Thr Glu Glu Arg Leu Lys
        275                 280                 285

Asn Val Leu Glu Ile Phe Gly Tyr Ile Ile His Ile Glu Tyr Lys Trp
    290                 295                 300

Ser Leu Asp Lys Trp Ser Tyr Ala Phe Ile Tyr Phe Ile Glu Glu Lys
305                 310                 315                 320

Cys Ala Ile Asn Ala Val Asn Ile Leu Asn Gln Lys Lys Phe Phe Asp
                325                 330                 335

Asn Ser Pro Asn His Lys Leu Ile Cys Phe Ile Val Ser Lys Gln Ile
            340                 345                 350

Pro Asn Gln Asn Thr Leu His Tyr Ser Lys Ala Asn Phe Ser Leu Leu
            355                 360                 365

Lys Asp Gly Pro Pro Gly Ala Asn Leu Phe Leu Tyr Gly Ile Pro Leu
370                 375                 380

Lys Trp Thr Glu Leu Asn Leu Ile Gln Leu Val Asn Lys Tyr Gly His
385                 390                 395                 400

Val Val Gly Leu Arg Ile Pro Tyr Ile Asn Asn Asp Asn Lys Lys
                405                 410                 415

Gln Gly Asn Arg Gly Phe Gly Phe Val Ser Tyr Asp Asn Lys Lys Ser
            420                 425                 430

Ala Val Glu Ala Phe Glu Leu Ser Lys Met Tyr Ile His Gly Lys
        435                 440                 445

Leu Leu Lys Val Gln Leu Lys Asn Gly Glu Glu Leu Glu Asn Leu Tyr
    450                 455                 460

Phe Gln Gly Val Glu His His His His His His
465                 470                 475

<210> SEQ ID NO 26
<211> LENGTH: 877
<212> TYPE: PRT
<213> ORGANISM: Artificial Sequence
<220> FEATURE:
<223> OTHER INFORMATION: PyPABP1-SpyTag

<400> SEQUENCE: 26

Gly Ser Ser Met Gly Met Ile Ala Asn Ser Thr Asn Ile Met Pro Pro
1               5                   10                  15

Ser Phe Ser Thr Ala Ser Leu Tyr Val Gly Asp Leu Ser Glu Asp Val
            20                  25                  30

Thr Glu Ala Val Leu Tyr Glu Ile Phe Asn Thr Val Gly His Val Leu
        35                  40                  45

Ser Ile Arg Val Cys Arg Asp Ser Val Thr Arg Lys Ser Leu Gly Tyr
    50                  55                  60

Ala Tyr Val Asn Tyr His Asn Leu Ala Asp Ala Glu Arg Ala Leu Asp
65                  70                  75                  80

Thr Leu Asn Tyr Thr Asn Ile Lys Gly Gln Pro Ala Arg Leu Met Trp
                85                  90                  95

Ser His Arg Asp Pro Ser Leu Arg Lys Ser Gly Thr Gly Asn Ile Phe
            100                 105                 110

Val Lys Asn Leu Asp Lys Thr Ile Asp Asn Lys Ala Leu Phe Asp Thr
        115                 120                 125

Phe Ser Met Phe Gly Asn Ile Leu Ser Cys Lys Val Ala Thr Asp Glu
    130                 135                 140

Phe Gly Lys Ser Lys Asn Tyr Gly Phe Val His Tyr Glu Asp Glu Glu
145                 150                 155                 160

Ser Ala Lys Glu Ala Ile Glu Lys Val Asn Gly Met Gln Leu Gly Ser
                165                 170                 175

Lys Asn Val Tyr Val Gly His Phe Ile Lys Ser Glu Arg Ala Thr
            180                 185                 190

Asn Asp Thr Lys Phe Thr Asn Leu Tyr Val Lys Asn Phe Pro Asp Thr
        195                 200                 205

Val Thr Glu Ala His Leu Lys Gln Leu Phe Ser Pro Tyr Gly Glu Ile
    210                 215                 220

Thr Ser Met Ile Val Lys Ser Asp Asn Lys Asn Arg Lys Phe Cys Phe
225                 230                 235                 240

-continued

```
Ile Asn Tyr Ser Asp Ala Asp Ser Ala Arg Asn Ala Met Glu Asn Leu
            245                 250                 255

Asn Gly Lys Lys Ile Thr Glu Asp Gly Lys Ile Asp Tyr Asn Tyr Asp
        260                 265                 270

Pro Lys Lys Glu Glu Thr Glu Lys Pro Ala Asn Glu Asn Ser Asn Asn
        275                 280                 285

Asn Thr Thr Thr Glu Glu Asn Thr Thr Thr Ser Glu Thr Pro Ala Glu
        290                 295                 300

Lys Lys Thr Pro Asp Ser Glu Pro Ala Thr Asn Lys Asp Ala Thr Pro
305                 310                 315                 320

Gly Glu Asp Gln Thr Ser Ala Asn Gly Thr Thr Thr Val Thr Ser
                325                 330                 335

Thr Thr Asp Ala Asn Pro Asp Ser Lys Thr Glu Glu Thr Pro Asn Asp
            340                 345                 350

Asn Thr Ala Asn Ala Gly Thr Asn Ala Ser Thr Thr Glu Lys Lys Asp
            355                 360                 365

Asn Lys Lys Ser Gly Glu Asn Thr Glu Thr Pro Asn Ile Leu Tyr Val
        370                 375                 380

Gly Pro His Gln Ser Arg Ala Arg Arg His Ala Ile Leu Lys Ala Lys
385                 390                 395                 400

Phe Asp Thr Leu Asn Thr Glu Ser Arg Asn Lys His Pro Gly Val Asn
                405                 410                 415

Leu Tyr Ile Lys Asn Leu Asp Asp Ser Met Asn Asp Gln Thr Leu Lys
            420                 425                 430

Glu Leu Phe Glu Pro Tyr Gly Thr Ile Thr Ser Ala Lys Val Met Lys
        435                 440                 445

Asp Asp Lys Asp Gln Ser Lys Gly Phe Gly Phe Val Cys Phe Gly Thr
450                 455                 460

His Glu Glu Ala Asn Lys Ala Val Thr Glu Met His Leu Lys Ile Ile
465                 470                 475                 480

Asn Gly Lys Pro Leu Tyr Val Gly Leu Ala Glu Lys Arg Glu Gln Arg
            485                 490                 495

Leu Ser Arg Leu Gln Gln Arg Phe Arg Met His Pro Ile Arg His His
        500                 505                 510

Ile Asn Asn Ala Leu Asn Ala Pro Ile Gln Tyr Pro Asn Ser Gln Thr
        515                 520                 525

Ala Gln Leu Gln Phe Asn Gln Asn Thr Leu Asn Tyr Gly Arg Pro Val
        530                 535                 540

Ile Thr Ser Phe Asn Gln Asn Leu Ile Ser Trp Arg His Gln Gln
545                 550                 555                 560

Ala Ala Ala Gln Gln Gln Ala Ala His Gln Ala Ala Ala Gln Gln
                565                 570                 575

Gln Leu Gly Phe Asn Gly Gly Leu Arg Gly Gln Ile Asn Gln Met Arg
        580                 585                 590

Leu Tyr Thr Gln Asn Asn Met Ile Asn His Asn Ile Gly Gln Asn Lys
        595                 600                 605

Ala Asn Gln Gln Leu His His Asn Gln Tyr Pro Ile Gly Pro Asn
        610                 615                 620

Pro Gln His Gln Gln Thr Asn Leu Asn Ala Pro Ala Gln Thr Asn Pro
625                 630                 635                 640

Gln Gln Leu Gln Gly Ala Ala Pro Val Pro Thr Asn Gln Leu Leu Asn
                645                 650                 655

Asn Asn Met Arg Asn Met Asn Ser Arg Gly Asn Arg Asn Leu Pro Gly
```

```
                660                 665                 670
Ile Asn Ile Gln Ser Pro Lys Gln Met Pro Leu Asn Met Val Gly Ala
            675                 680                 685

Lys Gln Thr Asn Pro Gln Gln Asn Gln Pro Gln Asn Gln Pro Gln Asn
        690                 695                 700

Gln Pro Gln Gly Gln Pro Asn Gln Pro Gln Lys Ser Gly Gln
705                 710                 715                 720

Ser Ile Gln Gln Gln Gln Gln Gln Gln Gln Thr Ile Pro Gln
                725                 730                 735

Asn Asn Asn Phe Lys Phe Thr Ser Gln Ala Arg Asn Arg Met Glu Leu
            740                 745                 750

Pro Asn Lys Asn Gly Asn Lys Val Asn Asn Met Thr Pro Gly Tyr Asn
        755                 760                 765

Asn Asn Thr Thr Leu Thr Ala Ala Leu Ala Ser Ala Pro Pro Ser
        770                 775                 780

Met Gln Lys Gln Val Leu Gly Glu Asn Leu Phe Pro Leu Val Ala Asn
785                 790                 795                 800

Tyr His Pro Thr Leu Ala Gly Lys Ile Thr Gly Met Met Leu Glu Met
                805                 810                 815

Asp Asn Ser Glu Leu Leu Ile Leu Leu Glu Asn Glu Asp Gln Leu Lys
            820                 825                 830

Lys Lys Ile Asp Glu Ala Leu Ala Val Leu Gln Asn Ala Lys Leu Glu
        835                 840                 845

Ala His Ile Val Met Val Asp Ala Tyr Lys Pro Thr Lys Val Glu Asn
    850                 855                 860

Leu Tyr Phe Gln Gly Val Glu His His His His His
865                 870                 875

<210> SEQ ID NO 27
<211> LENGTH: 155
<212> TYPE: PRT
<213> ORGANISM: Artificial Sequence
<220> FEATURE:
<223> OTHER INFORMATION: SpyTag-2xAP2

<400> SEQUENCE: 27

Gly Ser His Ser Ala His Ile Val Met Val Asp Ala Tyr Lys Pro Thr
1               5                   10                  15

Lys Ala Met Ile Gly Ser Gln Glu Pro Val Ile Leu Ile Asp Lys Ile
            20                  25                  30

Glu Arg Cys Leu Val Val Glu Trp Tyr Glu Asn Asn Ile Arg Arg Glu
        35                  40                  45

Gln Arg Ile Ser Tyr Lys Lys Tyr Gly Asn Asp Lys Ala Lys Leu Arg
    50                  55                  60

Ala Lys Glu Leu Ile Glu Lys Leu Lys Ser Gly Ile Thr Phe Glu Gln
65                  70                  75                  80

Leu Tyr Pro Asp Lys Gly Pro Pro Ile Val Arg Val Phe Glu Asn Val
                85                  90                  95

Gly Val Tyr Asn Val Ser Leu Ile Arg Asp Arg Ile Glu Arg Glu Trp
            100                 105                 110

Arg Val Glu Trp Leu Glu Asn Gly Val Pro Met Lys Ala Arg Trp Ser
        115                 120                 125

Cys Lys Lys Val Gly Asn Asp Glu Ala Gln Lys Arg Ala Asp Thr Phe
    130                 135                 140

Ala Gln Ser Met Ile Lys Gly Ile Phe Asn Pro
145                 150                 155
```

```
145            150            155
```

<210> SEQ ID NO 28
<211> LENGTH: 217
<212> TYPE: PRT
<213> ORGANISM: Artificial Sequence
<220> FEATURE:
<223> OTHER INFORMATION: SpyTag-TTP BD

<400> SEQUENCE: 28

```
Gly Ser His Ile Ala His Ile Val Met Val Asp Ala Tyr Lys Pro Thr
1               5                   10                  15

Lys His Met Asn Asn Asn Phe Asn Ile Asn Leu Gln Ile Glu Asp Gly
            20                  25                  30

Ile Thr Asn Lys Tyr Glu Ala Glu Val Asn Gly Tyr Phe Ala Lys Leu
        35                  40                  45

Tyr Thr Gly Glu Ile Thr Val Asn Thr Met Ile Asp Ile Met Lys Asn
50                  55                  60

Leu Ser Cys Ser Pro Lys Gly Ser Lys Asn Asn Asp Ile Tyr Lys Ser
65                  70                  75                  80

Met Leu Leu Ile Leu Phe Asn Glu Cys Lys Phe Phe Pro Lys Tyr Pro
                85                  90                  95

Val Glu Glu Leu Asp Ile Thr Ala Gln Leu Phe Gly Lys Leu Ile Lys
            100                 105                 110

His Asn Leu Leu Ile Ser Tyr Gly Asn Thr Leu Ser Val Val Leu Lys
        115                 120                 125

Cys Ile Leu Glu Ala Leu Lys Lys Gly Ser Asp Ser Lys Val Phe Asn
130                 135                 140

Phe Gly Ile Thr Ala Leu Glu Gln Phe Glu Asp Ser Leu Ile Cys Tyr
145                 150                 155                 160

Pro Ala Phe Leu Ser Ser Leu Ile Pro Leu Pro Thr Leu Arg Gln Tyr
                165                 170                 175

Asn Pro Gln Tyr Ile Ile His Cys Asn Glu Leu Leu Asn Thr Leu Pro
            180                 185                 190

Glu Gln Phe Arg Thr Leu Pro Tyr Ile Asp Ala Ser Thr Ile Leu Lys
        195                 200                 205

Ile Lys His Ile Ser Glu Ile Ser Ser
    210                 215
```

<210> SEQ ID NO 29
<211> LENGTH: 229
<212> TYPE: PRT
<213> ORGANISM: Artificial Sequence
<220> FEATURE:
<223> OTHER INFORMATION: SpyTag-UIS12

<400> SEQUENCE: 29

```
Gly Ser His Ile Ala His Ile Val Met Val Asp Ala Tyr Lys Pro Thr
1               5                   10                  15

Lys His Met Lys Asn Val Ile Ile Thr Asn Val Phe Leu Gly Asn Ile
            20                  25                  30

Pro Pro Asn Ile Thr Glu Glu Arg Leu Lys Asn Val Leu Glu Ile Phe
        35                  40                  45

Gly Tyr Ile Ile His Ile Glu Tyr Lys Trp Ser Leu Asp Lys Trp Ser
50                  55                  60

Tyr Ala Phe Ile Tyr Phe Ile Glu Glu Lys Cys Ala Ile Asn Ala Val
65                  70                  75                  80
```

-continued

```
Asn Ile Leu Asn Gln Lys Lys Phe Phe Asp Asn Ser Pro Asn His Lys
                85                      90                  95

Leu Ile Cys Phe Ile Val Ser Lys Gln Ile Pro Asn Gln Asn Thr Leu
            100                 105                 110

His Tyr Ser Lys Ala Asn Phe Ser Leu Leu Lys Asp Gly Pro Pro Gly
        115                 120                 125

Ala Asn Leu Phe Leu Tyr Gly Ile Pro Leu Lys Trp Thr Glu Leu Asn
    130                 135             140

Leu Ile Gln Leu Val Asn Lys Tyr Gly His Val Val Gly Leu Arg Ile
145                 150                 155                 160

Pro Tyr Ile Asn Asn Asp Asn Asp Lys Lys Gln Gly Asn Arg Gly Phe
                165             170                 175

Gly Phe Val Ser Tyr Asp Asn Lys Lys Ser Ala Val Glu Ala Phe Glu
            180             185                 190

Glu Leu Ser Lys Met Tyr Ile His Gly Lys Leu Leu Lys Val Gln Leu
        195                 200             205

Lys Asn Gly Glu Glu Leu Glu Asn Leu Tyr Phe Gln Gly Val Glu His
    210             215                 220

His His His His His
225
```

VERSATILE DISPLAY SCAFFOLDS FOR PROTEINS

CROSS REFERENCE TO RELATED APPLICATIONS

This application is a U.S. National Stage of PCT/US18/22803 filed Mar. 16, 2018 and which depends from and claims priority to U.S. Provisional Application No. 62/472,119 filed Mar. 16, 2017, the entire contents of each of which are incorporated herein by reference.

GOVERNMENT SUPPORT

This invention was made with government support under Grant No. GM125907 awarded by the National Institutes of Health. The Government has certain rights in the invention.

This application incorporates by reference a Sequence Listing with this application as an ASCII text file entitled "36PST88252WO_ST25_corrected" created on Dec. 30, 2019 having a size of 78,180 bytes.

FIELD

The disclosure relates to methods of cryo-electron microscopy and reagents useful for improved imaging of target molecules.

BACKGROUND

Revolutionary improvements have recently propelled Cryogenic Electron Microscopy (cryo-Electron Microscopy, Cryo-EM) to the front of the field of Structural Biology, with several structures now being reported at near atomic level resolution. However, there is a lower size limit of the molecules that can be imaged (~200 kilodaltons). As many macromolecules-of-interest are smaller than this, the use of Cryo-EM for structure determination has not be feasible for most people. Competing methods have genetically fused these proteins of interest to larger proteins to increase the overall protein size above the lower size limit. However, these scaffold proteins have not been sufficiently rigid or regular, required genetic fusions for each new protein-of-interest, and have only provided modest resolution of the structure of the protein-of-interest.

As such, new reagents and methods are needed for improved structural resolution of target molecules.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Provided are multimeric, self-assembling structures such as nanocages and processes utilizing them for obtaining biological and/or structural information about one or more target proteins. The processes capitalize on the power of cryo-electron microscopy or other system capable of resolving the presence or absence of a protein-protein interaction where solution structures of one or more target proteins are enhanced by bonding to an engineered nanocage with sufficient rigidity to allow its use as a source for solution of information of the target protein bound thereto.

A process includes associating a target protein with a multimeric self-assembling protein structure to form a target complex, and subjecting the target complex to cryo-electron microscopy, transmission electron microscopy, or combinations thereof, whereby the multimeric self-assembling protein structure serves as a scaffold for obtaining biological or structural information related to the target protein such as but not limited to solution of a three-dimensional structure of the target protein. In some aspects, the protein has a molecular weight of 200 kilodaltons or less. In some aspects, a value of resolution of said three-dimensional structure is less than 20 angstroms. Optionally, the protein has a molecular weight of 200 kilodaltons or less and a value of resolution of said three-dimensional structure is less than 20 angstroms. The multimeric self-assembling protein structure, the target protein, or both are or include optionally non-naturally occurring proteins in that at least one amino acid or other modification on the primary structure is not found in nature.

The multimeric self-assembling protein structure may include a plurality of protein substructures, wherein one or more of the protein substructures comprises a capture sequence, the capture sequence expressed at the N-terminus of the protein substructure or within 10 amino acids from the N-terminus of the protein substructure. In alternative aspects, the capture sequence may be expressed at the C-terminus of the protein substructure or within 10 amino acids from the C-terminus of the protein substructure. Optionally, the capture sequence may be expressed at both the N-terminus and the C-terminus of the protein substructure or within 10 amino acids from either respective terminus. In any of the forgoing aspects or combinations, the protein substructures may include a linker, a capture sequence, or both, the linker covalently bonding the capture sequence to the protein substructure. Optionally, each of said protein substructures is identical in primary amino acid sequence. Optionally, each of said protein substructures comprises an amino acid sequence that is 70% or greater identical to any one of SEQ ID NOs: 1-6. In any of the forgoing aspects, one or more of the protein substructures optionally includes a capture sequence, the capture sequence expressed at or near the N-terminus of the protein substructure, the capture sequence comprising the sequence of SEQ ID NO: 8, SEQ ID NO: 9, biotin, or avidin. Optionally, one or more of the protein substructures includes a linker and a capture sequence, the linker covalently bonding the capture sequence to the protein substructure, the linker a flexible linker or a rigid linker. Optionally, a linker sequence has portions that are flexible and other portions that are rigid. A flexible linker optionally includes a multimer of the amino acid sequence GGS, GSS, or combinations thereof. A rigid linker optionally includes one or more stabilizing disulfide bonds, one or more repeats of SEQ ID NO: 10, an amino acid sequence comprising 3 or more proline residues, an amino acid sequence comprising 1 or more sequences of PPA, or a combination thereof. In any of the forgoing or combinations thereof, the multimeric self-assembling protein structure includes or is a multimer of any one of SEQ ID NOs: 1-6. Optionally, the multimer is a 60-mer. Optionally, the multimeric self-assembling protein structure forms a dodecahedron.

One power of the provided processes and the materials used therein is the ability to gather biological information, structural information, or both on a target protein that has a molecular weight of 200 kDa or less. As such, in any of the foregoing aspects the target protein has a molecular weight of less than 200 kDa, optionally less than 150 kDa, optionally less than 120 kDa. A target protein optionally includes a tag, the tag optionally complementary to a capture sequence such that an association between the tag and the capture sequence may result in a tight bond between the two, optionally a covalent bond. As such, tag optionally includes or is SEQ ID NO: 20, SEQ ID NO: 21, biotin, or avidin. While virtually any target protein sequence may be used in the processes as provided herein, optionally a target protein sequence is or includes the RNA-binding protein, cytosolic Poly-A Binding Protein (PABP) (optionally SEQ ID NO: 16), a DNA-binding protein of the ApiAP2 specific transcription factor family (optionally SEQ ID NO: 17), a binding domain of tristetraprolin (TTP) of a NOT family protein (optionally SEQ ID NO: 18), or a RNA-recognition motif of the Upregulated in Infectious Sporozoites 12 (UIS12) protein (optionally SEQ ID NO: 19). A target protein may be saturated onto a multimeric self-assembling protein structure, optionally at a saturation level of 50% or greater, optionally 90% or greater. While knowledge in the art dictated that visualizing protein by processes such as cryo-electron microcoscopy must be done using samples with a salt concentration of 100 mM or less, it was found that salt concentration is not limited in the provided processes. As such, the multimeric self-assembling protein structure forms a target complex in an aqueous buffer including at or greater than 100 mM of a salt, optionally greater than 200 mM salt, optionally, from 200 mM salt to 500 mM salt. Using any of the forgoing aspects, in a process as provided herein structural information may be obtained of a target protein by cryo-electron microscopy, optionally to a value of resolution less than 10 Å, optionally less than 5 Å, optionally less than 3 Å. The value of resolution obtainable by the provided processes is sufficient to obtain biological or structural information of a target protein.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings, where like structure is indicated with like reference numerals and in which:

DETAILED DESCRIPTION

Figure 1A:
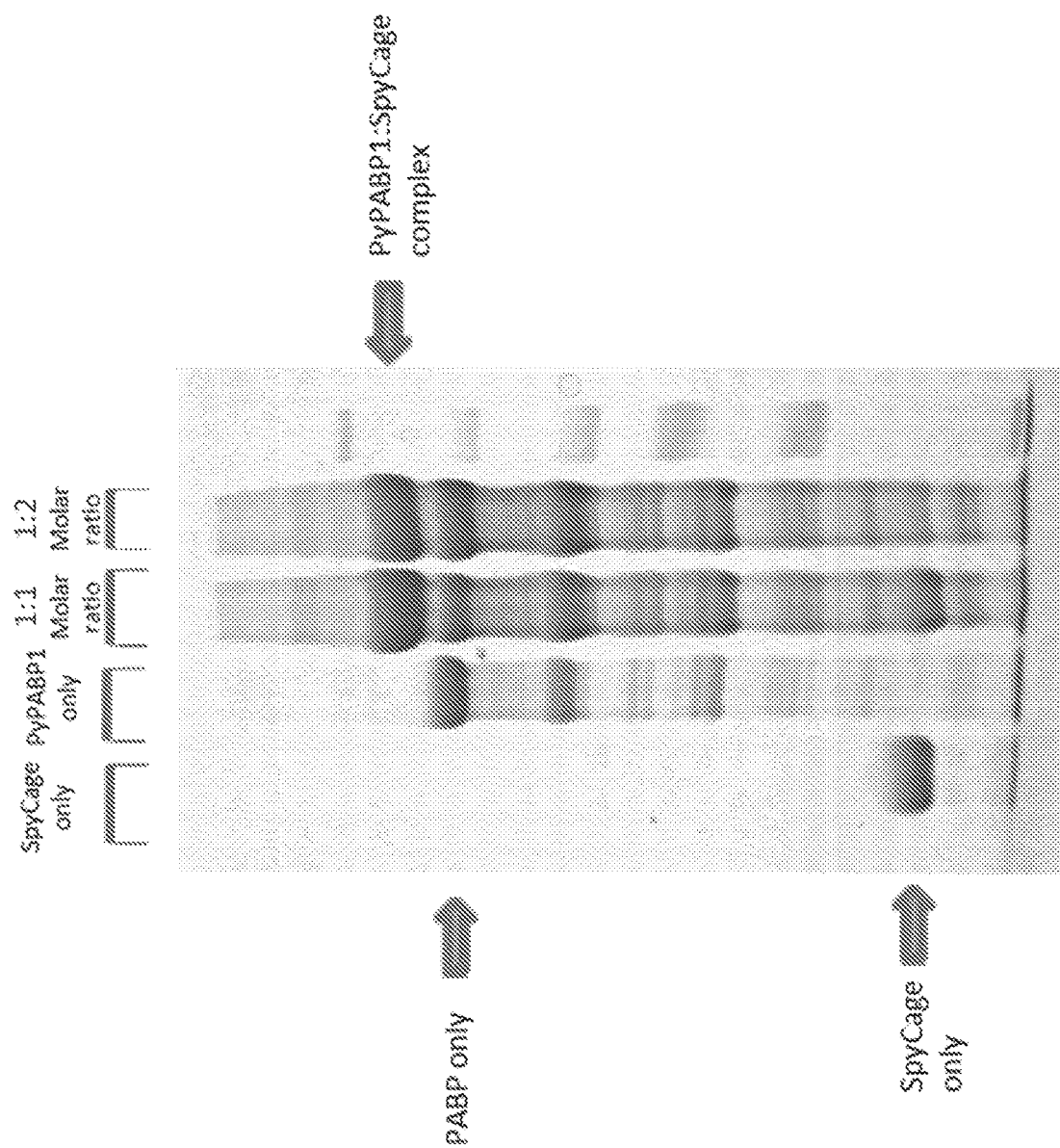
FIG. 1A illustrates the selective binding of PyPABP1 to nanocages at various molar ratios of components.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

A "protein" as used herein is an assembly of 2 or more amino acids linked by a peptide bond.

Provided are processes reagents that have utility for improved structure identification of target molecules. The processes capitalize on the power of cryo-electron microscopy (cryo-EM) and allow for structure solutions of target molecules having low molecular weights that were previously unsolvable by this method. By utilizing a relatively large and rigid protein structure that does not require genetic fusion with a target molecule, it was found that biological information can be solved with resolutions previously unattainable.

A process of solving a three-dimensional structure of a target protein as provided herein includes associating a target protein with a multimeric self-assembling protein structure (optionally non-naturally occurring) to form a target complex and subjecting the target complex to cryo-electron microscopy whereby the multimeric self-assembling protein structure serves as a scaffold for solution of the three-dimensional structure of the target protein. A multimeric protein structure as provided herein is a multimer of smaller proteins that assemble, optionally without the aid of external stimuli (self-assembling) to form the multimeric protein structure, optionally termed a "nanocage" in this disclosure. The smaller proteins are optionally protein substructures. The multimeric protein structure is the result of fusion of the protein substructures into a substantially rigid multimeric assembly suitable for use in cryo-electron microscopy.

The plurality of protein substructures self-assemble to form the multimeric protein structure. As is recognized in the art, self-assembly is the oligomerization of protein substructures into an ordered arrangement driven by non-covalent interactions. Such non-covalent interactions may be any of electrostatic interactions, π-interactions, van der Walls forces, hydrogen bonding, hydrophobic effects, or any combination thereof. The resulting multimeric protein structure is optionally ordered into a shape, illustratively an icosahedron, but others may be used as well such as those with tetrahedral or octahedral symmetry. Illustrative examples of such multimeric protein structures and how to make them are illustrated in WO 2016/138525 and U.S. Patent Application Publication No: 2015/0356240.

The number of protein substructures in a multimeric protein assembly is dependent on the overall arrangement. In some aspects, the number of protein substructures is 60 forming an icosahedron, however other structures with different numbers of substructures are similarly useful such as 24 protein subunit structures illustratively as that described by King, et al., Nature, 510, 103-108 (2014), or 12 protein subunit structures such as that described by King, et al., Science, 336, 1171-1174 (2012), 4-protein subunit structures illustratively as that described by Liu et al. Proceedings of the National Academy of the Sciences (in press) doi:http://dx.doi.org/10.1101/212233.

It is appreciated that in some aspects all protein substructures may be identical in primary sequence thereby promoting identity in structure to form a homomultimeric protein structure. However, there may be some structures where two or more different protein substructures are used. Optionally, 2, 3, 4, 5, or more different protein substructures may be used to form the multimeric protein structure.

Optionally, the protein substructures are forms of aldolase protein, optionally structurally modified so as to either alter self-assembly properties, increase rigidity of the final multimeric structure, to express one or more tags for purification, to express one or more tags for associating with a target protein or combinations thereof. In some aspects, the protein substructures are one or more of those described by Hsia, et al., Nature, 2016; 535:136-147 or those designed and described in WO 2016/138525A1 with either optionally modified otherwise as described herein.

Optionally, a protein substructure includes the primary sequence as defined in SEQ ID NO: 1 (MEELFKKHKIVAVLRANSVEEAKKKALAVFLGGVHLIEITFTVPDADTVIKELSFLKEM GAIIGAGTVTSVEQCRKAVESGAEFIVSPHLDEEISQFCKEKGVFYMPGVMTPTELVKA MKLGHTILKLFPGEVVGPQFVKAMKGPFPNVKFVPTGGVNLDNVCEWFKAGVLAVGV GSALVKGTPVEVAEKAKAFVEKIRGCTEHM), optionally SEQ ID NO: 2 (MEELFKKHKIVAVLRANSVEEAKKKALAVFLGGVHLIEITFTVPDADTVIKELSFLKEM GAIIGAGTVTSVEQCRKAVESGAEFIVSPHLDEEISQFCKEKGVFYMPGVMTPTELVKA MKLGHTILKLFPGEVVGPQFVKAMKGPFPNVKFVPTGGVNLDNVCEWFKAGVLAVGV GSALVKGTPVEVAEKAKAFVEKIRGCTEHM), optionally SEQ ID NO: 3 (FKKHKIVAVLRANSVEEAKKKALAVFLGGVHLIEITFTVPDADTVIKELSFLKEMGAIIG AGTVTSVEQCRKAVESGAEFIVSPHLDEEISQFCKEKGVFYMPGVMTPTELVKAMKLGH TILKLFPGEVVGPQFVKAMKGPFPNVKFVPTGGVNLDNVCEWFKAGVLAVGVSALV KGTPVEVAEKAKAFVEKIRGCTEHM). In some aspects, a protein substructure further includes additional residues at an N or C terminus that may be due to translations from endonuclease restriction sites, tags such as for purification (e.g. 6×His tag), a specific protease cleavage site such as a thrombin cleavage site, or other suitable modification. In some aspects, the protein substructures include the primary sequence of SEQ ID NO: 4 (MKMEELFKKHKIVAVLRANSVEEAKKKALAVFLGGVHLIEITFTVPDADTVIKELSFLK EMGAIIGAGTVTSVEQCRKAVESGAEFIVSPHLDEEISQFCKEKGVFYMPGVMTPTELVK AMKLGHTILKLFPGEVVGPQFVKAMKGPFPNVKFVPTGGVNLDNVCEWFKAGVLAVG VGSALVKGTPVEVAEKAKAFVEKIRGCTEHM), SEQ ID NO: 5 (ASMEELFKKHKIVAVLRANSVEEAKKKALAVFLGGVHLIEITFTVPDADTVIKELSFLKE MGAIIGAGTVTSVEQCRKAVESGAEFIVSPHLDEEISQFCKEKGVFYMPGVMTPTELVK AMKLGHTILKLFPGEVVGPQFVKAMKGPFPNVKFVPTGGVNLDNVCEWFKAGVLAVG VGSALVKGTPVEVAEKAKAFVEKIRGCTEHM) or SEQ ID NO: 6 (EELFKKHKIVAVLRANSVEEAKKKALAVFLGGVHLIEITFTVPDADTVIKELSFLKEMG AIIGAGTVTSVEQCRKAVESGAEFIVSPHLDEEISQFCKEKGVFYMPGVMTPTELVKAM KLGHTILKLFPGEVVGPQFVKAMKGPFPNVKFVPTGGVNLDNVCEWFKAGVLAVGV SALVKGTPVEVAEKAKAFVEKIRGCTEHM).

The protein substructures are optionally modified at one or more amino acid positions relative to any one or more of SEQ ID Nos: 1-6. Optionally, the protein substructures are 70% identical or greater to any one or more of SEQ ID Nos: 1-6, optionally 75% or more identical, optionally 80% or more identical, optionally 85% or more identical, optionally 90% or more identical, optionally 95% or more identical, optionally 96% or more identical, optionally 97% or more identical, optionally 98% or more identical, optionally 99% or more identical. Illustrative residues that may be substituted include E26K, E33L, K61M, D187V and R190A. Optionally, other substitutions may be made such as deletion of any of the first 10 residues at the N- or C-termini of the protein substructures. In some aspects, an extra M is added to the N-terminus so as to extend the alpha helical structure, optionally into an alpha helical linker as described herein.

Modifications and changes can be made in the structure of the protein substructure primary sequences that are the subject of the application and still obtain a molecule having similar characteristics as the original such as similar self-assembly properties, similar rigidity to the final multimeric structure, or other. Such substitutions are optionally conservative amino acid substitutions. For example, certain amino acids can be substituted for other amino acids in a sequence without appreciable alteration of desired properties. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 are optional, those within ±1 are optional preferred, and those within ±0.5 are optional.

Substitution of like amino acids can also be made on the basis of hydrophilicity, particularly, where the biological functional equivalent polypeptide or peptide thereby created is intended for use in particular aspects as described herein. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Aspects of this disclosure thus contemplate functional or biological equivalents of a polypeptide as set forth above. In particular, aspects of the polypeptides can include variants having about 50%, 60%, 70%, 80%, 90%, and 95% sequence identity to the polypeptide of interest.

One or more of the protein substructures is optionally modified at the N-terminus, the C-terminus or both with one or more of a linker, a capture sequence, or both. One power of the present invention is the ability to create self-assembling proteins structures that express capture sequences oriented either out and away from the multimeric structure such as through an N-terminal capture sequence, directed into the core of the multimeric structure such as through a C-terminal capture sequence or both. A capture sequence may be located directly at the N- or C-terminus, or within 10 amino acids from the N- or C-terminus, optionally in substitution of or within 10 amino acids of the N- or C-terminus of any one or more of SEQ ID Nos: 1-6.

One advantage of a capture sequence is that it eliminates the need for genetic fusions of target proteins-of-interest for construction of the multimeric self-assembling protein structure. For example, prior preparations of nanocages with a protein used as a label required that the monomers be recombinantly expressed already fused to the target protein-of-interest, increasing complexity of making the materials as well as reducing the likelihood of success. The use of a capture sequence that can pair with a tag sequence on a target protein-of-interest increases the robustness of the resulting nanocage, but also allows for adjustment of parameters such as saturation of target protein on the nanocage that were found to improve the resulting overall structure solution by cryo-electron microscopy.

As such, a protein substructure optionally includes one or more capture sequences. Illustrative examples of a capture sequence include those that allow specific recognition of the capture sequence by the tag on the target protein and lead to covalent bonding of the two, optionally through the use of a spontaneous isopeptide bond. Optionally, a tag terminates with an alkylamine or other functional group that can pair with a tag on a target sequence. Optionally, the tag on the target sequence terminates in a carboxylic acid allowing isopeptide bond formation with the capture sequence. This results in robust covalent bonding between the nanocage and the target protein of interest.

In some aspects, a capture sequence is or includes biotin, avidin, SEQ ID NO: 7 (GSGDSATHIKFSKRDEDGKELA-GATMELRDSSGKTISTWISDGQVKDFYLYPGKY-TFVE TAAPDGYEVATAITFTVNEQGQVTVNGKATKG-DAHIGVD), SEQ ID NO: 8 (MGSSHHHHHHGSGD-SATHIKFSKRDEDGKELAGATMELRDSSGKTISTWI-SDGQVKDF YLYPGKYTFVETAAPDGYEVATAITFTV-NEQGQVTVNGKATKGDAHIGVD), SEQ ID NO: 9 (MKPLRGAVFSLQKQHPDYPDIYGAIDQNGTYQ-NVRTGEDGKLTFKNLSDGKYRLFENS EPAGYKPV-QNKPIVAFQIVNGEVRDVTSIVPQDIPATYEFTNGK-HYITNEPIPPK), any functional portion thereof, a nucleic acid (e.g., deoxyribonucleic acid, or ribonucleic acid) sequence, or other such suitable capture sequence. A suitable capture sequence is one that will bind, either covalently or non-covalently, and specifically with a tag or other desired portion of a target molecule.

In some aspects one or more protein substructure of a multimeric self-assembling protein structure includes a linker, the linker bound to the protein substructure and the capture sequence, optionally between the protein substructure and the capture sequence. The linker optionally covalently or non-covalently (e.g. hydrogen bonding, van der Walls forces, hydrophobic effects, electrostatic interactions, π-interactions, or combinations thereof), or both, binds the protein substructure to the capture sequence.

A linker is optionally a protein linker, single amino acid, nucleic acid based linker such as one or more nucleotides (e.g., ribonucleotides, deoxyribonucleotide), a nucleic acid of two or more nucleotides, a substituted or unsubstituted alkyl, akenyl, or alkynyl of 1-20 carbons, or other suitable structure. Optionally, a linker is a flexible linker or a rigid linker. A flexible linker is one that is not restricted by interlinker bonding or regular three dimensional structure in an aqueous environment at 25° C. A rigid linker is one that includes one or more interlinker bonds (either covalent or non-covalent) (e.g. electrostatic interaction, disulfide bond, or other) or forms a secondary structure (e.g. alpha helix, beta sheet, beta turn, omega loop) that is stable in an aqueous environment at 25° C.

Optionally, a linker is a protein linker of two or more amino acids. Illustrative protein linkers include, but are not limited to one or more multimers of the sequence GGS, GSS, PPA, SEQ ID NO: 10, a proline residue, or combinations thereof. A multimer of any of the forgoing optionally include 2, 3, 4, 5, 6, 7, 8, 9, or more repeats or substitutions of the foregoing. In specific examples, a linker has a sequence of 5 repeats of GGS, 5 repeats of GSS, 5 or more linked GGS and GSS sequences in any order, 5 repeats of SEQ ID NO: 10, a 9-mer of proline residues, a 3-mer of the sequence PPA, or any combination thereof.

As such, a protein substructure optionally includes a self-assembling monomer protein, a linker, and a capture sequence where the linker and the capture sequence are optionally bound to the self-assembling monomer at the N-terminus, the C-terminus, or both. Illustrative examples of protein substructures include but are not limited to those of SEQ ID NO: 11 (MGSSHHHHHHGSGDSATHIKFSKRDEDGKELAGATMELRDSSGKTISTWISDGQVKDF YLYPGKYTFVETAAPDGYEVATAITFTVNEQGQVTVNGKATKGDAHIGVDHHHHHHG GSGGSGGSGGSMKMEELFKKHKIVAVLRANSVEEAKKKALAVFLGGVHLIEITFTVPDA DTVIKELSFLKEMGAIIGAGTVTSVEQCRKAVESGAEFIVSPHLDEEISQFCKEKGVFYMP GVMTPTELVKAMKLGHTILKLFPGEVVGPQFVKAMKGPFPNVKFVPTGGVNLDNVCE WFKAGVLAVGVGSALVKGTPVEVAEKAKAFVEKIRGCTEHM), SEQ ID NO: 12 (MGSSHHHHHHGSGDSATHIKFSKRDEDGKELAGATMELRDSSGKTISTWISDGQVKDF YLYPGKYTFVETAAPDGYEVATAITFTVNEQGQVTVNGKATKGDAHIGVDEAAAKEAA AKEAAAKEAAAKEAAAKASMEELFKKHKIVAVLRANSVEEAKKKALAVFLGGVHLIEI TFTVPDADTVIKELSFLKEMGAIIGAGTVTSVEQCRKAVESGAEFIVSPHLDEEISQFCKE KGVFYMPGVMTPTELVKAMKLGHTILKLFPGEVVGPQFVKAMKGPFPNVKFVPTGGV NLDNVCEWFKAGVLAVGVGSALVKGTPVEVAEKAKAFVEKIRGCTEHM), SEQ ID NO: 13. (MGSSHHHHHHGSGDSATHIKFSKRDEDGKELAGATMELRDSSGKTISTWISDGQVKDF YLYPGKYTFVETAAPDGYEVATAITFTVNEQGQVTVNGKATKGDAHIGVDEAAAKEAA AKEAAAKEAAAKEAAAKEELFKKHKIVAVLRANSVEEAKKKALAVFLGGVHLIEITFT VPDADTVIKELSFLKEMGAIIGAGTVTSVEQCRKAVESGAEFIVSPHLDEEISQFCKEKGV FYMPGVMTPTELVKAMKLGHTILKLFPGEVVGPQFVKAMKGPFPNVKFVPTGGVNLDN VCEWFKAGVLAVGVGSALVKGTPVEVAEKAKAFVEKIRGCTEHM), SEQ ID NO: 14 (MGSSHHHHHHGSGDSATHIKFSKRDEDGKELAGATMELRDSSGKTISTWISDGQVKDF YLYPGKYTFVETAAPDGYEVATAITFTVNEQGQVTVNGKATKGDAHIGVDPPPPPPPPP EELFKKHKIVAVLRANSVEEAKKKALAVFLGGVHLIEITFTVPDADTVIKELSFLKEMGA IIGAGTVTSVEQCRKAVESGAEFIVSPHLDEEISQFCKEKGVFYMPGVMTPTELVKAMKL GHTILKLFPGEVVGPQFVKAMKGPFPNVKFVPTGGVNLDNVCEWFKAGVLAVGVGSA LVKGTPVEVAEKAKAFVEKIRGCTEHM), or SEQ ID NO: 15 (MGSSHHHHHHGSGDSATHIKFSKRDEDGKELAGATMELRDSSGKTISTWISDGQVKDF YLYPGKYTFVETAAPDGYEVATAITFTVNEQGQVTVNGKATKGDAHIGVDPPAPPAPPA EELFKKHKIVAVLRANSVEEAKKKALAVFLGGVHLIEITFTVPDADTVIKELSFLKEMGA IIGAGTVTSVEQCRKAVESGAEFIVSPHLDEEISQFCKEKGVFYMPGVMTPTELVKAMKL GHTILKLFPGEVVGPQFVKAMKGPFPNVKFVPTGGVNLDNVCEWFKAGVLAVGVGSA LVKGTPVEVAEKAKAFVEKIRGCTEHM). It is appreciated based on the teachings provided herein and the skill of one in the art that modifications of any of the aforementioned sequences are similarly suitable. Illustratively, a protein substructure is optionally 70% or more identical to any one of SEQ ID Nos: 11-15, optionally 80% or more identical to any one of SEQ ID Nos: 11-15, optionally 90% or more identical to any one of SEQ ID Nos: 11-15, optionally 95% or more identical to any one of SEQ ID Nos: 11-15, optionally 96% or more identical to any one of SEQ ID Nos: 11-15, optionally 97% or more identical to any one of SEQ ID Nos: 11-15, optionally 98% or more identical to any one of SEQ ID Nos: 11-15, optionally 99% or more identical to any one of SEQ ID Nos: 11-15.

A multimeric self-assembling protein structure that expresses a capture sequence is capable of binding, optionally specifically binding, a target protein. Due to the rigidity and regularity of the multimeric self-assembling protein structure, the compositions and processes are able to provide biological or structural information of a target protein when analyzed by cryo-electron microscopy. Cryo-electron microscopy is undergoing a sea change in its ability to deliver such biological and structural information concerning a protein of interest. Atomic resolution structures with low or no symmetry now represent the fastest growing group of structures submitted to the EM database. The vast majority of these structures, however, have a molecular weight of 200 kilodaltons (kDa) or greater. The molecular mass size restriction of >200 kDa for successful cryo-EM structures achieved previously is largely due to the high noise and low contrast of unstained biological samples embedded in vitrified buffer. It was found by the inventors of this disclosure that the use of multimeric self-assembling protein structures as provided herein are capable of delivering resolution (≤20 Å) information of molecules with a molecular mass of less than 200 kDa.

As such, a target protein as used in the processes or compositions as provided herein is optionally a protein with a molecular weight in kDa at or less than 200, optionally 190, optionally 180, optionally 170, optionally 160, optionally 150, optionally 140, optionally 130, optionally 120, optionally 110, optionally 100, or lower. In specific aspects, a target protein has a molecular weight of 150 kDa or less. In other aspects, a target protein has a molecular weight of 120 kDa or less. It is appreciated that the molecular weight of a target protein as used herein is the calculated molecular weight of the protein free of post translational modifications such as glycosylation, phosphorylation, sulfonation, or other. The molecular weight of a target protein as used herein is the molecular weight absent a tag, purification sequence, or both.

Illustrative specific examples of target proteins include those of the RNA-binding protein, cytosolic Poly-A Binding Protein (PABP), a DNA-binding protein of the ApiAP2 specific transcription factor family, a binding domain of tristetraprolin (TTP) of a NOT family protein, or a RNA-recognition motif of the Upregulated in Infectious Sporozoites 12 (UIS12) protein, among others. It is appreciated that the identity, primary sequence, secondary structure, tertiary structure, posttranslational modification, or function of a target protein is independent of the ability of the processes as provided herein to provide biological or structural information about the structural protein by cryo-electron microscopy.

Specific examples of target proteins are those provided in SEQ ID NO: 16 (MTMSPILGYWKIKGLVQPTRLLLEYLEEKYEEHLYERDEGDKWRNKKFELGLEFPNLP YYIDGDVKLTQSMAIIRYIADKHNMLGGCPKERAEISMLEGAVLDIRYGVSRIAYSKDFE TLKVDFLSKLPEMLKMFEDRLCHKTYLNGDHVTHPDFMLYDALDVVLYMDPMCLDAF PKLVCFKKRIEAIPQIDKYLKSSKYIAWPLQGWQATFGGGDHPPKSDLVPRGSSMGMIA NSTNIMPPSFSTASLYVGDLSEDVTEAVLYEIFNTVGHVLSIRVCRDSVTRKSLGYAYVN YHNLADAERALDTLNYTNIKGQPARLMWSHRDPSLRKSGTGNIFVKNLDKTIDNKALF DTFSMFGNILSCKVATDEFGKSKNYGFVHYEDEESAKEAIEKVNGMQLGSKNVYVGHFI KKSERATNDTKFTNLYVKNFPDTVTEAHLKQLFSPYGEITSMIVKSDNKNRKFCFINYSD ADSARNAMENLNGKKITEDGKIDYNYDPKKEETEKPANENSNNNTTTEENTTTSETPAE KKTPDSEPATNKDATPGEDQTSANGTTTTVTSTTDANPDSKTEETPNDNTANAGTNAST TEKKDNKKSGENTETPNILYVGPHQSRARRHAILKAKFDTLNTESRNKHPGVNLYIKNL DDSMNDQTLKELFEPYGTITSAKVMKDDKDQSKGFGFVCFGTHEEANKAVTEMHLKII NGKPLYVGLAEKREQRLSRLQQRFRMHPIRHHINNALNAPIQYPNSQTAQLQFNQNTLN YGRPVITSFNQNNLISWRHQQAAAQQQAAHQQAAAQQQLGFNGGLRGQINQMRLYTQ NNMINHNIGQNKANQQLHHNQQYPIGPNPQHQQTNLNAPAQTNPQQLQGAAPVPTNQL LNNNMRNMNSRGNRNLPGINIQSPKQMPLNMVGAKQTNPQQNQPQNQPQNQPQGQPQ NQPQQKSGQSIQQQQQQQQQQTIPQNNNFKFTSQARNRMELPNKNGNKVNNMTPGYN NNTTLTAAALASAPPSMQKQVLGENLFPLVANYHPTLAGKITGMMLEMDNSELLILLEN EDQLKKKIDEALAVLQNAK), SEQ ID NO: 17 (IGSQEPVILIDKIERCLVVEWYENNIRREQRISYKKYGNDKAKLRAKELIEKLKSGITFEQ LYPDKGPPIVRVFENVGVYNVSLIRDRIEREWRVEWLENGVPMKARWSCKKVGNDEAQ KRADTFAQSMIKGIFNP), SEQ ID NO: 18 (NNNFNINLQIEDGITNKYEAEVNGYFAKLYTGEITVNTMIDIMKNLSCSPKGSKNNDIYK SMLLILFNECKFFPKYPVEELDITAQLFGKLIKHNLLISYGNTLSVVLKCILEALKKGSDS KVFNFGITALEQFEDSLICYPAFLSSLIPLPTLRQYNPQYIIHCNELLNTLPEQFRTLPYIDA STILKIKHISEISS), SEQ ID NO: 19 (KNVIITNVFLGNIPPNITEERLKNVLEIFGYIIHIEYKWSLDKWSYAFIYFIEEKCAINAVNI LNQKKFFDNSPNHKLICFIVSKQIPNQNTLHYSKANFSLLKDGPPGANLFLYGIPLKWTE LNLIQLVNKYGHVVGLRIPYINNDNDKKQGNRGFGFVSYDNKKSAVEAFEELSKMYIH GKLLKVQLKNGEE), or other sequence, or modification thereof.

The target protein optionally is a modification of a wild-type sequence such that the target protein is non-naturally occurring. Such modifications include the addition, subtraction or substitution or one or more amino acids optionally for the purpose of including an endonuclease restriction site, a site to add or remove a post-translational modification, or a tag for purification or labeling purposes (e.g. 6×His tag, GST tag, addition of a fluorophore, etc.), among other reasons known in the art for protein identification, labeling, localization, purification, etc.

A target protein optionally includes one or more tags that are complementary to a capture sequence on a substructure protein. Complementary in this sense means that the tag will bind to, optionally specifically bind to, the capture sequence, optionally with high affinity. The specific localization of the target protein to the capture sequence allows the use of the resulting complex in cryo-electron microscopy to gather biological or structural information about the target protein. A target protein optionally includes 1 tag, optionally 2 or more tags. A tag is optionally a multimeric or repeating amino acid or nucleic acid sequence, a vitamin, or other suitable tag sequence. Illustrative examples of a tag on a target protein includes but are not limited to avidin, biotin, SEQ ID NO: 20 (AHIVMVDAYKPTK), or SEQ ID NO: 21 (KLGDIEFIKVNKG). It should be recognized that SEQ ID NO: 20 is a complementary tag to the capture sequence of SEQ ID NO: 7 in that the two sequences will self-associate to form a complex that is then auto-linked by a covalent bond between a lysine on one unit and an aspartic acid on the other unit to form an isopeptide bond. Similarly, tag sequence SEQ ID NO: 21 is complementary to capture sequence SEQ ID NO: 9 where a complex is formed that results in the formation of a covalent linkage between the tag and the capture sequence. Similar and specific high affinity interactions are optionally observed between avidin and biotin where a substructure protein is labeled with either avidin or biotin, and the target protein is labeled with the complementary tag of either biotin or avidin.

A target protein optionally includes 1 tag, optionally 2 tags, optionally 3 tags. A tag is optionally localized to an N-terminal end, a C-terminal end, an intermediate position, or other. Optionally, a target protein is expressed with one or more tags within the peptide sequence and is exposed at the N-terminal end or C-terminal end by cleavage of a portion of the protein sequence by a protease.

Target proteins, similar to substructure proteins, are optionally produced by recombinant DNA expression efforts as recognized in the art. As such, a target protein sequence optionally includes one or more of an extra amino acid or multiple amino acids resulting from the insertion of a restriction endonuclease cleave site in the DNA, one or more protease cleavage sites, and one or more purification tags. A target protein may be coexpressed with associated purification tags, modifications, other proteins such as in a fusion peptide, or other modifications or combinations as recognized in the art. Illustrative purification tags include 6×His, FLAG, biotin, ubiquitin, SUMO, or other tag known in the art. A purification tag is illustratively cleavable such as by linking to a target protein via an enzyme cleavage sequence that is cleavable by an enzyme known in the art illustratively including Factor Xa, thrombin, SUMOstar protein, or trypsin. It is further appreciated that chemical cleavage is similarly operable with an appropriate cleavable linker.

Illustrative specific examples of target proteins as expressed by recombinant DNA efforts include for illustration purposes only and are not limited to SEQ ID NO: 22 (MTMSPILGYWKIKGLVQPTRLLLEYLEEKYEEHLYERDEGDKWRNKKFELGLEFPNLP YYIDGDVKLTQSMAIIRYIADKHNMLGGCPKERAEISMLEGAVLDIRYGVSRIAYSKDFE TLKVDFLSKLPEMLKMFE- DRLCHKTYLNGDHVTHPDFMLYDALDVVLYMD-
PMCLDAF PKLVCFKKRIEAIPQIDKYLKSSKYIAWPL-
QGWQATFGGGDHPPKSDLVPRGSSMGMIA NST-
NIMPPSFSTASLYVGDLSEDVTEAVLYEIFNTVGHVL-
SIRVCRDSVTRKSLGYAYVN YHNLADAERALDTL-
NYTNIKGQPARLMWSHRDPSLRKSGTGNIFVKNL-
DKTIDNKALF DTFSMFGNILSCKVATDEFGKSKNY-
GFVHYEDEESAKEAIEKVNGMQLGSKNVYVGHFI
KKSERATNDTKFTNLYVKNFPDTVTEAHLKQLFSPY-
GEITSMIVKSDNKNRKFCFINYSD ADSARNAMENL-
NGKKITEDGKIDYNYDPKKEETEKPANENSNNNTT-
TEENTTTSETPAE KKTPDSEPATNKDATPGEDQT-
SANGTTTTVTSTTDANPDSKTEETPNDNTANAGT-
NAST TEKKDNKKSGENTETPNILYVGPHQS-
RARRHAILKAKFDTLNTESRNKHPGVNLYIKNL DDS-
MNDQTLKELFEPYGTITSAKVMKDDKDQS-
KGFGFVCFGTHEEANKAVTEMHLKII NGKPLYVG-
LAEKREQRLSRLQQRFRMHPIRHHINNALNAPIQY-
PNSQTAQLQFNQNTLN YGRPVITSFNQNNLISWRH-
QQAAAQQQAAHQQAAAQQQLGFNGGLRGQIN-
QMRLYTQ NNMINHNIGQNKANQQLHHNQQYP-
IGPNPQHQQTNLNAPAQTNPQQLQGAAPVPTNQL
LNNNMRNMNSRGNRNLPGINIQSPKQMPLNM-
VGAKQTNPQQNQPQNQPQNQPQGQPQ NQPQQKS-
GQSIQQQQQQQQQQTIPQNNNFKFTSQARNRMEL-
PNKNGNKVNNMTPGYN NNTTLTAAALASAPPS-
MQKQVLGENLFPLVANYHPTLAGKITGMMLEMDN-
SELLILLEN EDQLKKKIDEALAVLQNAKLEAHIVMV-
DAYKPTKVENLYFQGVEHHHHHH), SEQ ID NO: 23
(MSPILGYWKIKGLVQPTRLLLEYLEEKYEEHLYER-
DEGDKWRNKKFELGLEFPNLPYYI DGDVKLTQS-
MAIIRYIADKHNMLGGCPKERAEISMLEGAVLDIRY-
GVSRIAYSKDFETLK VDFLSKLPEMLKMFEDRLC-
HKTYLNGDHVTHPDFMLYDALDVVLYMDPMC-
LDAFPKL VCFKKRIEAIPQIDKYLKSSKYIAWPLQG-
WQATFGGGDHPPKSDLVPRGSHSAHIVMVD AYKP-
TKAMIGSQEPVILIDKIERCLVVEWYENNIRREQRI-
SYKKYGNDKAKLRAKELIEK LKSGITFEQLYPDKGP-
PIVRVFENVGVYNVSLIRDRIEREWRVEWLENGV-
PMKARWSCK KVGNDEAQKRADTFAQSMIKGIFNP),
SEQ ID NO: 24 (MTMSPILGYWKIKGLVQPTRLLLEY-
LEEKYEEHLYERDEGDKWRNKKFELGLEFPNLP YYI-
DGDVKLTQSMAIIRYIADKHNMLGGCPKERAEISM-
LEGAVLDIRYGVSRIAYSKDFE TLKVDFLSKLPEML-
KMFEDRLCHKTYLNGDHVTHPDFMLYDALDVVL-
YMDPMCLDAF PKLVCFKKRIEAIPQIDKYLKSSKY-
IAWPLQGWQATFGGGDHPPKSDLVPRGSSMGSSH
HHHHHSSGLVPRGSHIAHIVMVDAYKPTKHMN-
NNFNINLQIEDGITNKYEAEVNGYFAK LYTGEITVNT-
MIDIMKNLSCSPKGSKNNDIYKSMLLILFNECKF-
FPKYPVEELDITAQLFG KLIKHNLLISYGNTLSVV-
LKCILEALKKGSDSKVFNFGITALEQFEDSLICYPAF-
LSSLIPLP TLRQYNPQYIIHCNELLNTLPEQFRTLPYI-
DASTILKIKHISEISS), SEQ ID NO: 25
(MTMSPILGYWKIKGLVQPTRLLLEYLEEKYEEHLY-
ERDEGDKWRNKKFELGLEFPNLP YYIDGDVKLTQS-
MAIIRYIADKHNMLGGCPKERAEISMLEGAVLDIR-
YGVSRIAYSKDFE TLKVDFLSKLPEMLKMFEDRL-
CHKTYLNGDHVTHPDFMLYDALDVVLYMDPMC-
LDAF PKLVCFKKRIEAIPQIDKYLKSSKYIAWPLQ-
GWQATFGGGDHPPKSDLVPRGSSMGSSH HHHH-
HSSGLVPRGSHIAHIVMVDAYKPTKHMKNVIITN-
VFLGNIPPNITEERLKNVLEIFG YIIHIEYKWSLDK-
WSYAFIYFIEEKCAINAVNILNQKKFFDNSPNHK-
LICFIVSKQIPNQNT LHYSKANFSLLKDGPPGANL-
FLYGIPLKWTELNLIQLVNKYGHVVGLRIPYINND-
NDKK QGNRGFGFVSYDNKKSAVEAFEELSKMYI-
HGKLLKVQLKNGEELENLYFQGVEHHHHH H). It is
appreciated that modifications of any of the forgoing such as
by substitution of a tag, a purification tag, localization of a
tag, a purification tag, or protease cleave site are well within
the level of skill in the art and presented under this disclosure. Any of the aforementioned substitutions of amino acids
above are equally applicable to a target protein and incorporated herein by reference.

A substructure protein, target protein, or any portion
thereof, optionally further including a purification tag,
linker, capture sequence, protease cleavage site, or other, are
optionally formed by recombinant DNA expression methods. The identification of codon sequences in DNA/RNA
from a known protein sequence are readily achieved by
persons of ordinary skill in the art. Protein expression is
illustratively accomplished from transcription of desired
nucleic acid sequence, translation of RNA transcribed from
desired nucleic acid sequence, modifications thereof, or
fragments thereof. Protein expression is optionally performed in a cell based system such as in *E. coli*, HeLa cells,
or Chinese hamster ovary cells. Bacterial cells such as *E.
coli* are commonly used, but if post-translational modifications are desired on one or more of a target protein, protein
substructure or both may be expressed in a mammalian cell.
It is appreciated that cell-free expression systems are similarly operable.

It is recognized that numerous variants, analogues, or
homologues are within the scope of the present invention
including amino acid substitutions, alterations, modifications, or other amino acid changes that increase, decrease, or
do not alter the function of the substructure protein sequence
or target protein sequence. Several post-translational modifications are similarly envisioned as within the scope of the
present invention illustratively including incorporation of a
non-naturally occurring amino acid, phosphorylation, glycosylation, addition of pendent groups such as biotinylation,
fluorophores, lumiphores, radioactive groups, antigens, or
other molecules.

A method is also provided for recombinantly expressing
a protein substructure or target protein nucleic acid or
protein sequence or fragments thereof wherein a cell is
transformed with a desired nucleic acid sequence and cultured under suitable conditions that permit expression of the
protein substructure or target protein nucleic acid sequence
or protein either within the cell or secreted from the cell. Cell
culture conditions are particular to cell type and expression
vector. Culture conditions for particular vectors and cell
types are within the level of skill in the art to design and
implement without undue experimentation.

Recombinant or non-recombinant proteinase peptides or
recombinant or non-recombinant proteinase inhibitor peptides or other non-peptide proteinase inhibitors can also be
used in the expression of a substructure protein or target
protein. Proteinase inhibitors are optionally modified to
resist degradation, for example degradation by digestive
enzymes and conditions. Techniques for the expression and
purification of recombinant proteins are known in the art
(see Sambrook Eds., Molecular Cloning: A Laboratory
Manual 3$^{rd}$ ed. (Cold Spring Harbor, N.Y. 2001).

Some aspects of the present invention are compositions
containing protein substructure (e.g., 13-01 substructure
protein) or target protein nucleic acid that can be expressed
as encoded polypeptides or proteins. The engineering of
DNA segment(s) for expression in a prokaryotic or eukaryotic system may be performed by techniques generally
known to those of skill in recombinant expression. It is believed that virtually any expression system may be employed in the expression of the claimed nucleic and amino sequences.

Generally speaking, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene (e.g. target protein) where desired.

As used herein, the terms "engineered" and "recombinant" cells are synonymous with "host" cells and are intended to refer to a cell into which an exogenous DNA segment or gene, such as a cDNA or gene has been introduced. Therefore, engineered cells are distinguishable from naturally occurring cells that do not contain a recombinantly introduced exogenous DNA segment or gene. A host cell is optionally a naturally occurring cell that is transformed with an exogenous DNA segment or gene or a cell that is not modified. A host cell preferably does not possess a naturally occurring gene encoding or similar to a target protein or protein substructure. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded polypeptide in accordance with the present invention one would prepare an expression vector that comprises a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli*.chi. 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation sites, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful both because both are obtained easily from the virus as a fragment that also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly(A) addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

It is contemplated that the isolated nucleic acids of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

Further aspects of the present disclosure concern the purification, and in particular embodiments, the substantial purification, of an encoded protein or peptide. The term "purified" or "isolated" protein or peptide as used herein, is intended to refer to a composition, isolatable from other components, wherein the protein or peptide is purified to any degree relative to its naturally-obtainable state, i.e., in this case, relative to its purity within a cell of a tick salivary gland. A purified protein or peptide therefore also refers to a protein or peptide, free from the environment in which it may naturally occur.

Generally, "purified" or "isolated" will refer to a protein or peptide composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure as based on knowledge in the art. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., *Biochem. Biophys. Res. Comm.*, 76:425, 1977). It will therefore be appreciated that under differing electrophoresis conditions, the apparent molecular weights of purified or partially purified expression products may vary.

Methods of obtaining a target protein or protein substructure illustratively include isolation of target protein or protein substructure from a host cell or host cell medium. Methods of protein isolation illustratively include column chromatography, affinity chromatography, gel electrophoresis, filtration, or other methods known in the art. Optionally, target protein or protein substructure is expressed with a tag operable for affinity purification. As described above, optionally, a purification tag is a 6×His tag. A 6×His tagged protein is illustratively purified by Ni-NTA column chromatography or using an anti-6×His tag antibody fused to a solid support. (Geneway Biogech, San Diego, Calif.) Other tags and purification systems are similarly operable.

It is appreciated that a target protein or protein substructure is optionally not tagged. Purification is optionally achieved by methods known in the art illustratively including ion-exchange chromatography, affinity chromatography using anti-target protein or substructure protein antibodies, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

A target protein, protein substructure, or fragment thereof is optionally chemically synthesized. Methods of chemical synthesis have produced proteins greater than 600 amino acids in length with or without the inclusion of modifications such as glycosylation and phosphorylation. Methods of chemical protein and peptide synthesis illustratively include solid phase protein chemical synthesis. Illustrative methods of chemical protein synthesis are reviewed by Miranda, L P, *Peptide Science,* 2000, 55:217-26 and Kochendoerfer G G, *Curr Opin Drug Discov Devel.* 2001; 4(2):205-14, the contents of which are incorporated herein by reference.

As discussed above, one or more protein substructures includes a capture sequence. Optionally, all protein substructures include a capture sequence. As such, many aspects a multimeric self-assembling protein structure includes a plurality of capture domains available for association with a target protein. The number of protein substructures that include a capture sequence or the number of bound target proteins to a multimeric self-assembling protein structure relative to the total number of such sites available is a target protein saturation level. A saturation level is optionally 1% or greater, optionally 1.6% or greater, optionally 5% or greater, optionally 10% or greater, optionally 20% or greater, optionally 30% or greater, optionally 40% or greater, optionally 50% or greater, optionally 60% or greater, optionally 70% or greater, optionally 80% or greater, optionally 90% or greater, optionally 99% or greater, optionally 100%.

For successful solution structure or gathering of biological information using cryo-electron microscopy, it was historically believed that the concentration of salt in the buffer system a target is employed in should be less than 200 millimolar (mM). It was discovered using the presently provided processes and materials that the level of salt could be either raised or lowered depending on the desired level of detail in the solution structure and the target protein being analyzed. As such, some aspects of a provided process include salt in the buffer system at a level of 1 mM to 500 mM, or greater, or any value or range there between. Optionally the level of salt is 1 mM or greater, optionally 10 mM or greater, optionally 50 mM or greater, optionally 100 mM or greater, optionally 200 mM or greater, optionally 300 mM or greater, optionally 400 mM or greater, optionally 500 mM or greater. Optionally, the level of salt is 200 mM to 500 mM, optionally 300 mM to 500 mM.

Processes as provided herein include subjecting the target complex that includes the target protein associated with a multimeric self-assembling protein structure to analyses by cryo-electron microscopy. The use of cryo-electron microscopy to solve protein structures is known in the art and any suitable device typically employed for analysis of protein, nucleic acid, or other target by cryo-electron microscopy are suitable for use in the processes of this disclosure. Methods of cryo-electron microscopy are optionally described by Bai, et al, *Trends in biochemical sciences,* 2015; 40(1):49-57, Kimanius, et al, *eLife,* 2016; 5, Kuhlbrand, *eLife,* 2014; 3:e03678, McMullan, et al., *Methods Enzymol,* 2016; 579: 1-17, and Scheres, *eLife,* 2014; 3:e03665.

Cryo-electron microscopy was unexpectedly found to be produce solution structures or biological information of high resolution using the materials and processes as provided herein when analyzing target proteins of low molecular weight, such as 200 kDa or below, or other molecular weight as provided herein. It is typically considered that valuable information about a target protein can be gathered at a resolution with a value of 20 Å or lower. As such, a process optionally produces a three-dimensional structure of a target protein to a value of resolution of 20 Å or lower, optionally 18 Å or lower, optionally 15 Å or lower, optionally 12 Å or lower, optionally 10 Å or lower, optionally 9 Å or lower, optionally 8 Å or lower, optionally 7 Å or lower, optionally 6 Å or lower, optionally 5 Å or lower, optionally 4 Å or lower, optionally 3 Å or lower, optionally 2 Å or lower, optionally 1 Å or lower.

The provided processes and materials as described herein streamline the entire process of cryo-electron microscopy and other applications by allowing the decoration of a pre-purified protein "nanocage" with the protein-of-interest that bears a capture tag (e.g., SpyTag, SnoopTag, AviTag, respectively) or in the case of the use of monomeric streptavidin as the capture domain, with any molecule-of-interest that is biotinylated, optionally uniformly biotinylated. Uncaptured molecules-of-interest are simply dialyzed away.

These protein substructures or self-assembled multimeric structures can easily be used alone or as part of a kit for cryo-electron microscopy applications or immunization applications (as it concentrates antigen). These allow for orthologous capture systems that use covalent or high affinity non-covalent bonds. This can also allow for the capture of proteins with commonly used epitope tags by use of an adapter molecule with the monomeric streptavidin capture domain (which binds to biotin).

EXAMPLES

Example 1

Production of Protein Substructures and Multimers Thereof

Recodonized sequences that expresses the capture sequence of SEQ ID NO: 7, a linker, and the 13-01 scaffold (SEQ ID NO: 1) (together SEQ ID NOs: 11-15) were each ligated into a modified pET28b+ expression vector, and incorporates a 6×His epitope tag near its N-terminus. Linking the 13-01 scaffold and the capture sequence is accomplished through either direct binding or through a flexible (4×GGS) or rigid (EAAAK (SEQ ID NO: 10), 9×Pro, 3×PPA) protein linker. The recombinant protein was expressed in CodonPlus(DE3) strain of *E. coli* grown in 1-3 L of LB broth in shaker flasks. To produce the soluble protein, the culture was grown to an $OD_{600}$ of 0.6 and protein expression was induced by addition of 0.5 mM IPTG (final concentration) and incubated at 37° C. for 3 hours. The cell pellet was suspended in T500 pH 8.0 Solution (20 mM Tris-Cl pH 8.0@RT, 500 mM NaCl, 1 mM DTT, 1 mM benzamidine, and 10% v/v glycerol) and lysed by 4 rounds of sonication (Per round, 30 pulses at 60% amplitude and 50% duty cycle (Model 450 Branson Digital Sonifier, Disruptor Horn). The crude extract was spun at 15500×g for 10 minutes at 4° C. The supernatant was incubated with 5 ml of Ni-NTA resin (Thermo Scientific, Cat #88223) equilibrated in T500 pH 8.0 Solution on a nutator for 1 hour at 4° C. The resin was washed with 10 CV T500 pH 8.0 Solution, and protein was eluted using a linear gradient from 0-100% B over 10 CV (Buffer A: T500 pH 8.0 Solution; Buffer B: T500 pH 8.0 Solution+300 mM imidazole). The elution pool was then dialyzed into T100 pH 8.5 Solution (20 mM Tris-Cl pH 8.5 @RT, 100 mM NaCl, 1 mM DTT, and 10% v/v glycerol). The individual protein substructures self-assembled into a plurality of multimeric nanoages. To further purify the nanocages, anion exchange chromatography was performed using a 20 mL bed volume of Q-Sepharose resin that was equilibrated in T100 pH 8.5 Solution (Buffer A). The column was then washed using 3 CV Buffer A, and nanocages were eluted using a linear gradient from 0-100% Buffer B (20 mM Tris-Cl pH 8.5 @RT, 1000 mM NaCl, 1 mM DTT, and 10% v/v glycerol) over 20 CV. The elution pool was exhaustively dialyzed into 20 mM Tris pH 8.0 @RT, 100 mM NaCl, 1 mM DTT, and 10% glycerol. Lastly, the purified nanocage was concentrated to 2-5 mg/ml using Amicon Ultra Centrifugal Filters (Fisher Scientific Cat #UFC9-003-08).

Example 2

Target Protein Expression

Full length PyPABP1 (PY17X_1441700, AA1-835) was ligated into a modified pET28b+ expression vector that may or may not incorporate a GST tag on the N-terminus and a tag and 6×His purification tag on the C-terminus of the expressed protein, which can be cleaved with thrombin and TEV protease, respectively. The recombinant protein was expressed in the Rosetta2 (DE3) pLysS strain of *E. coli* grown in 20 L LB broth using a 30 L fermenter. To produce soluble protein, the culture was grown to an $OD_{600}$ of 0.6, and protein expression was induced by addition of 0.2 mM IPTG (final concentration) and incubated at 21° C. for 17 hr. The cell pellet was suspended in Low Imidazole Buffer (25 mM Tris-Cl pH 7.5 @RT, 500 mM NaCl, 10 mM imidazole, 1 mM DTT, 1 mM benzamidine, and 10% v/v glycerol) and lysed by 10 rounds of sonication (each round consisting of 20 pulses at 30% amplitude and 50% duty cycle (Model 450 Branson Digital Sonifier, Disruptor Horn)). The crude extract was spun at 15500×g for 10 minutes at 4° C. The supernatant was incubated with 5 ml of Ni-NTA resin (Thermo Scientific, Cat #88223) equilibrated in Low Imidazole Buffer on a nutator for 1 hour at 4° C. The resin was washed with 4 CV Mid Imidazole Buffer (25 mM Tris-Cl pH 7.5 @RT, 500 mM NaCl, 50 mM imidazole, 1 mM DTT, 1 mM benzamidine, and 10% v/v glycerol), and PyPABP1-SpyTag was then eluted using a linear gradient from 0-100% B over 15 CV (Buffer A: 25 mM Tris-Cl pH 7.5 @RT, 500 mM NaCl, 10 mM imidazole, 1 mM DTT, 1 mM benzamidine, and 10% v/v glycerol; Buffer B: 25 mM Tris-Cl pH 7.5 @RT, 500 mM NaCl, 300 mM imidazole, 1 mM DTT, 1 mM benzamidine, and 10% v/v glycerol). The pooled elution fractions containing the recombinant protein were dialyzed into 10 mM HEPES pH 6.74 @RT, 100 mM NaCl, 1 mM DTT, 1 mM benzamidine, and 10% v/v glycerol. Next, PyPABP1-SpyTag was purified further using cation exchange chromatography using a 20 mL bed volume of SP-Sepharose resin that was equilibrated in Buffer A (Buffer A: 10 mM HEPES pH 6.74 @RT, 100 mM NaCl, 1 mM DTT, 1 mM benzamidine, and 10% v/v glycerol). The column was then washed using 3 CV Buffer A then eluted using a linear gradient from 0-50% B (Buffer B: 10 mM HEPES pH 6.74 @RT, 1000 mM NaCl, 1 mM DTT, 1 mM benzamidine, and 10% v/v glycerol) over 20 CV. The elution fractions containing the recombinant protein were pooled and exhaustively dialyzed into 20 mM MES pH 6.0 @RT, 100 mM NaCl, 100 mM $MgCl_2$, 1 mM DTT, and 10% v/v glycerol. Lastly, the purified protein was concentrated to 10-12 mg/ml using Amicon Ultra Centrifugal Filters (Fisher Scientific Cat #UFC9-003-08). The resulting protein has the primary sequence of the GST tagged PyPABP1-SpyTag is SEQ ID NO: 22 and the non-GST tagged sequence is SEQ ID NO: 26

(GSSMGMIANSTNIMPPSFSTASLYVGDLSEDVTEAVLYEIFNTVGHVLSI

RVCRDSVTRKSLGYAYVNYHNLADAERALDTLNYTNIKGQPARLMWSHRDP

SLRKSGTGNIFVKNLDKTIDNKALFDTFSMFGNILSCKVATDEFGKSKNYG

FVHYEDEESAKEAIEKVNGMQLGSKNVYVGHFIKKSERATNDTKFTNLYVK

NFPDTVTEAHLKQLFSPYGEITSMIVKSDNKNRKFCFINYSDADSARNAME

NLNGKKITEDGKIDYNYDPKKEETEKPANENSNNNTTTEENTTTSETPAEK

KTPDSEPATNKDATPGEDQTSANGTTTTVTSTTDANPDSKTEETPNDNTAN

AGTNASTTEKKDNKKSGENTETPNILYVGPHQSRARRHAILKAKFDTLNTE

SRNKHPGVNLYIKNLDDSMNDQTLKELFEPYGTITSAKVMKDDKDQSKGFG

FVCFGTHEEANKAVTEMHLKIINGKPLYVGLAEKREQRLSRLQQRFRMHPI

RHHINNALNAPIQYPNSQTAQLQFNQNTLNYGRPVITSFNQNNLISWRHQQ

AAAQQQAAHQQAAAQQQLGFNGGLRGQINQMRLYTQNNMINHNIGQNKANQ

QLHHNQQYPIGPNPQHQQTNLNAPAQTNPQQLQGAAPVPTNQLLNNNMRNM

NSRGNRNLPGINIQSPKQMPLNMVGAKQTNPQQNQPQNQPQNQPQGQPQNQ

PQQKSGQSIQQQQQQQQQQTIPQNNNFKFTSQARNRMELPNKNGNKVNNMT

PGYNNNTTLTAAALASAPPSMQKQVLGENLFPLVANYHPTLAGKITGMMLE

MDNSELLILLENEDQLKKKIDEALAVLQNAKLEAHIVMVDAYKPTKVENLY

FQGVEHHHHHH).

The sequence expressing 2×AP2 DNA binding domain (PF3D7_0604100, AA177-312) was ligated into a modified pET28b+ expression vector which incorporates a GST purification tag and tag SEQ ID NO: 20 on the N-terminus. To remove the GST purification tag, a thrombin protease site was incorporated in between GST purification tag and SEQ ID NO: 20. The recombinant protein was expressed in CodonPlus(DE3) strain of E. coli grown in 3 L of LB broth in shaker flasks. To produce the soluble protein, the culture was grown to an $OD_{600}$ of 0.6, and protein expression was induced by addition of 0.5 mM IPTG (final concentration) and incubated at 23° C. for 18 hrs. The cell pellet was suspended in GST Lysis Buffer (50 mM Tris-Cl pH 8.0 @RT, 150 mM NaCl, 1 mM DTT, 1 mM benzamidine, and 10% v/v glycerol) and lysed by 4 rounds of sonication (each round consisting of 30 pulses at 60% amplitude and 50% duty cycle (Model 450 Branson Digital Sonifier, Disruptor Horn)). The crude extract was spun at 15500×g for 10 minutes at 4° C. The supernatant was incubated with 4 ml of Glutathione Agarose resin (Thermo Scientific, Cat #PI16101) equilibrated in GST Lysis Buffer on a nutator for 1 hour at 4° C. The resin was washed with 10 CV GST Lysis Buffer then eluted using 10 CV GST Elution Buffer (50 mM Tris-Cl pH 8.0 @RT, 150 mM NaCl, 20 mM reduced glutathione, 1 mM DTT, 1 mM benzamidine, and 10% v/v glycerol). To remove the GST tag, thrombin was added to the elution pool to a final concentration of 10 units/ml to permit digestion for 18 hours at 4° C. To purify the target protein further, cation exchange chromatography was performed using a 20 mL bed volume of SP-Sepharose resin that was equilibrated in Buffer A (20 mM HEPES pH 7.5 @RT, 100 mM NaCl, 1 mM DTT, and 10% v/v glycerol). The column was then washed using 3 CV Buffer A then eluted using a linear gradient from 0-100% Buffer B (20 mM HEPES pH 7.5 @RT, 1000 mM NaCl, 1 mM DTT, and 10% v/v glycerol) over 20 CV. Lastly, the purified target protein was concentrated to 2-5 mg/ml using Amicon Ultra Centrifugal Filters (Fisher Scientific Cat #UFC9-003-08). The resulting target protein is SEQ ID NO: 27

(GSHSAHIVMVDAYKPTKAMIGSQEPVILIDKIERCLVVEWYENNIRREQR

ISYKKYGNDKAKLRAKELIEKLKSGITFEQLYPDKGPPIVRVFENVGVYNV

SLIRDRIEREWRVEWLENGVPMKARWSCKKVGNDEAQKRADTFAQSMIKGI

FNP).

The sequence expressing a putative TTP-binding domain (PY17X_0945600, AA1-199) was ligated into a modified pET28b+ expression vector which incorporates a GST tag, 6×His, and SEQ ID NO: 20 on the N-terminus. To remove the GST tag and 6×His, a thrombin protease site was incorporated in between 6×His and the SEQ ID NO: 20 sequences. The recombinant protein was expressed in CodonPlus(DE3) strain of E. coli grown in 8 L of LB broth in shaker flasks. To produce the soluble protein, the culture was grown to an $OD_{600}$ of 0.6, and protein expression was induced by addition of 0.5 mM IPTG (final concentration) and incubated at 18° C. for 18 hrs. The cell pellet was suspended in GST Lysis Buffer (50 mM Tris-Cl pH 8.0 @RT, 150 mM NaCl, 1 mM DTT, 1 mM benzamidine, and 10% v/v glycerol) and lysed by 4 rounds of sonication (each round consisting of 30 pulses at 60% amplitude and 50% duty cycle (Model 450 Branson Digital Sonifier, Disruptor Horn)). The crude extract was spun at 15500×g for 10 minutes at 4° C. The supernatant was passed over a 5 ml of Glutathione Agarose resin (Thermo Scientific, Cat #PI16101) column that was equilibrated in GST Lysis Buffer. The resin was washed with 10 CV GST Lysis Buffer then eluted using 5 CV GST Elution Buffer (50 mM Tris-Cl pH 8.0 @RT, 150 mM NaCl, 20 mM reduced glutathione, 1 mM DTT, 1 mM benzamidine, and 10% v/v glycerol). To remove the GST and 6×His tags, thrombin was added to the elution pool to a final concentration of 10 units/ml to permit digestion for 18 hours at 4° C. while dialyzing into 20 mM HEPES pH 6.76, 150 mM NaCl, 1 mM DTT, and 10% glycerol. To purify target protein further, cation exchange chromatography was performed using a 20 mL bed volume of SP-Sepharose resin that was equilibrated in Buffer A (20 mM HEPES pH 6.76 @RT, 75 mM NaCl, 1 mM DTT, and 10% v/v glycerol). The column was then washed using 3 CV Buffer A then eluted using a linear gradient from 0-100% Buffer B (20 mM HEPES pH 6.76 @RT, 1000 mM NaCl, 1 mM DTT, and 10% v/v glycerol) over 20 CV. The elution pool was adjusted to 20 mM HEPES pH 6.76 @RT, 400 mM NaCl, 1 mM DTT, and 10% v/v glycerol. Lastly, the purified target protein was concentrated to ~1 mg/ml using Amicon Ultra Centrifugal Filters (Fisher Scientific Cat #UFC9-003-08). The resulting purified target protein had the sequence of SEQ ID NO: 28

(GSHIAHIVMVDAYKPTKHMNNNFNINLQIEDGITNKYEAEVNGYFAKLYT
GEITVNTMIDIMKNLSCSPKGSKNNDIYKSMLLILFNECKFFPKYPVEELD
ITAQLFGKLIKHNLLISYGNTLSVVLKCILEALKKGSDSKVFNFGITALEQ
FEDSLICYPAFLSSLIPLPTLRQYNPQYIIHCNELLNTLPEQFRTLPYIDA
STILKIKHISEISS).

The sequence expressing UIS12 RNA recognition motifs 1 and 2 (PY17X_0507300, AA246-439) was ligated into a modified pET28b+ expression vector which incorporates a GST tag, 6×His tag, and SEQ ID NO: 20 on the N-terminus, and a 6×His tag on the C-terminus. To remove the N-terminal GST and 6×His tags, a thrombin protease site was incorporated in between 6×His and the SpyTag sequences. The recombinant protein was expressed in CodonPlus(DE3) strain of *E. coli* grown in 3 L of LB broth in shaker flasks. To produce the soluble protein, the culture was grown to an $OD_{600}$ of 0.6, and protein expression was induced by addition of 0.5 mM IPTG (final concentration) and incubated at 23° C. for 18 hrs. The cell pellet was suspended in Low Imidazole Buffer (25 mM Tris-Cl pH 7.5 @RT, 500 mM NaCl, 10 mM imidazole, 1 mM DTT, 1 mM benzamidine, and 10% v/v glycerol) and lysed by 4 rounds of sonication (each round consisting of 30 pulses at 60% amplitude and 50% duty cycle (Model 450 Branson Digital Sonifier, Disruptor Horn)). The crude extract was spun at 15500×g for 10 minutes at 4° C. The supernatant was incubated with 5 ml of Ni-NTA resin (Thermo Scientific, Cat #88223) equilibrated in Low Imidazole Buffer on a nutator for 1 hour at 4° C. The resin was washed with 10 CV Low Imidazole Buffer, then 4 CV Mid Imidazole Buffer (25 mM Tris-Cl pH 7.5 @RT, 500 mM NaCl, 50 mM imidazole, 1 mM DTT, 1 mM benzamidine, and 10% v/v glycerol), and finally eluted with 6 CV of High Imidazole Buffer (25 mM Tris-Cl pH 7.5 @RT, 500 mM NaCl, 300 mM imidazole, 1 mM DTT, 1 mM benzamidine, and 10% v/v glycerol). To remove the N-terminal GST tag and 6×His, thrombin was added to the elution pool to a final concentration of 10 units/ml to permit digestion for 18 hours at 4° C. while dialyzing into 20 mM HEPES pH 7.5, 100 mM NaCl, 1 mM DTT, and 10% v/v glycerol. To purify the target protein further, cation exchange chromatography was performed using a 20 mL bed volume of SP-Sepharose resin that was equilibrated in Buffer A (20 mM HEPES pH 7.5 @RT, 100 mM NaCl, 1 mM DTT, and 10% v/v glycerol). The column was then washed using 3 CV Buffer A then eluted using a linear gradient from 0-100% Buffer B (20 mM HEPES pH 7.5 @RT, 1000 mM NaCl, 1 mM DTT, and 10% v/v glycerol) over 20 CV. The elution pool was exhaustively dialyzed into 20 mM HEPES pH 7.5 @RT, 400 mM NaCl, 1 mM DTT, and 10% v/v glycerol. Lastly, the purified protein was concentrated to ~0.5 mg/ml using Amicon Ultra Centrifugal Filters (Fisher Scientific Cat #UFC9-003-08). The resulting target protein has a sequence of SEQ ID NO: 29

(GSHIAHIVMVDAYKPTKHMKNVIITNVFLGNIPPNITEERLKNVLEIFGY
IIHIEYKWSLDKWSYAFIYFIEEKCAINAVNILNQKKFFDNSPNHKLICFI

-continued
VSKQIPNQNTLHYSKANFSLLKDGPPGANLFLYGIPLKWTELNLIQLVNKY
GHVVGLRIPYINNDNDKKQGNRGFGFVSYDNKKSAVEAFEELSKMYIHGKL
LKVQLKNGEELENLYFQGVEHHHHHH).

Example 3

Loading Multimeric Self-Assembling Protein Structures with Target Protein

Figure 1B:
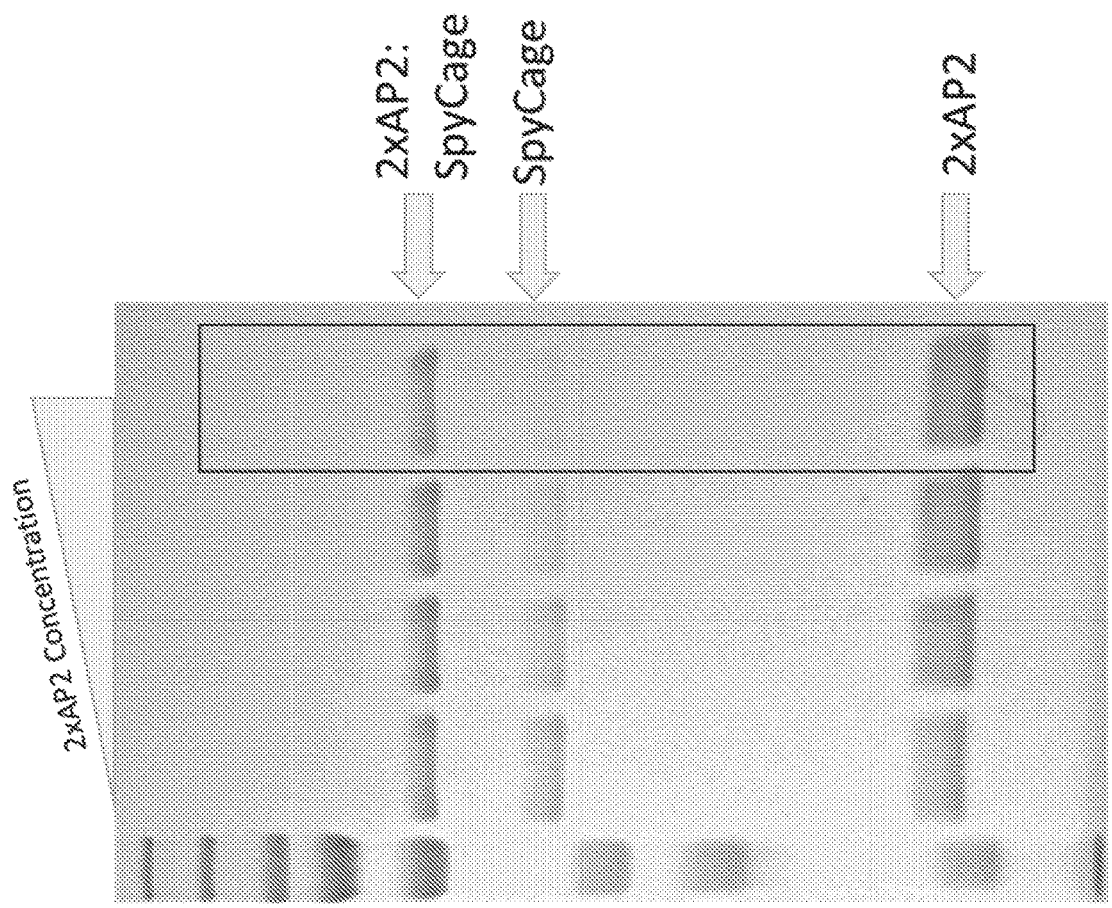
FIG. 1B illustrates the selective binding of 2×AP2 to nanocages at various molar ratios of components.
Figure 1C:
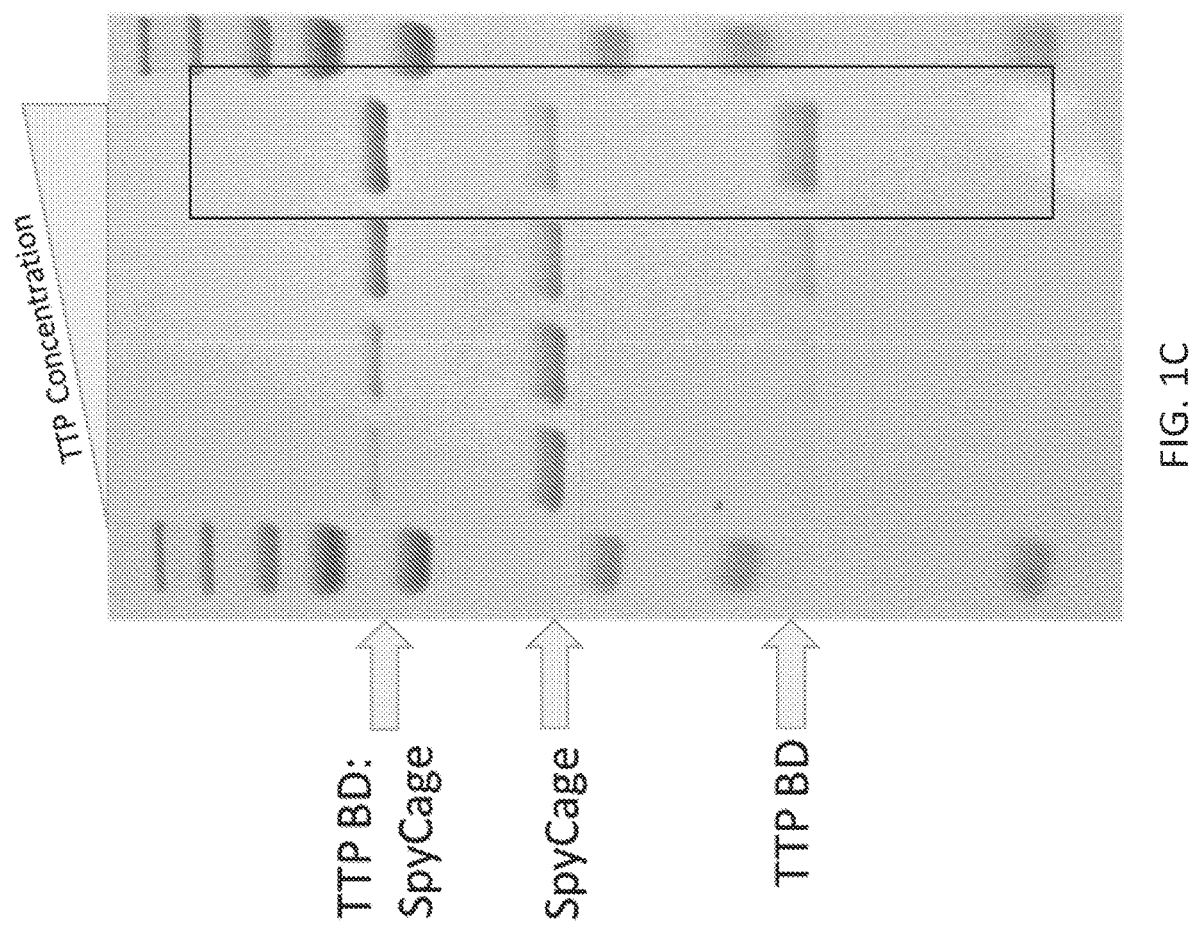
FIG. 1C illustrates the selective binding of TTP to nanocages at various molar ratios of components.
Figure 1D:
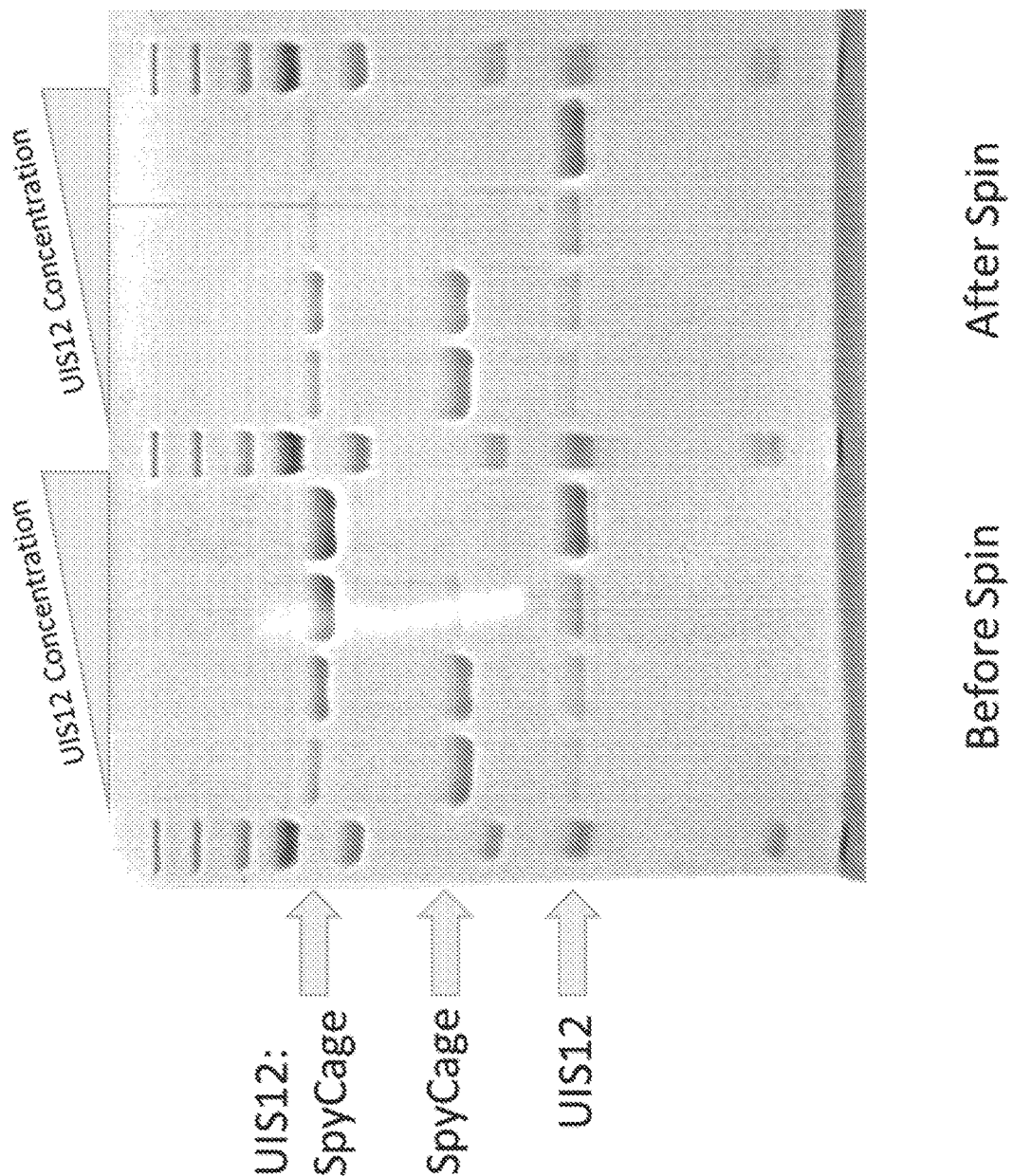
FIG. 1D illustrates the selective binding of UIS12 to nanocages at various molar ratios of components.

To determine a desirable molar ratio of multimeric structures to target protein-of-interest, different degrees of saturation of the nanocages were performed by a titration experiment, in which the concentration of multimer is kept constant while the concentration of the target protein-of-interest is varied. Target proteins of PyPABP1, AP2, TTP BD, and UIS12 were tested. The standard buffer condition is 20 mM Tris-Cl pH 8.0 @RT, 100 mM NaCl, 1 mM DTT. The standard molar ratios that are tested are molar concentration ratios of 1:0.2, 1:0.5, 1:1, 1:2, 1:3, 1:4, and 1:5 protein substructure monomer to target protein with a final concentration of protein substructure monomer between 0.2-1 mg/ml. The reactions are performed at room temperature for 2-3 hours depending on the rate of each independent reaction, which can vary depending on the protein-of-interest. The extent of saturation of the multimer nanocages is determined using SDS-PAGE, as binding of a protein-of-interest produces a covalent bond with the scaffold protein, and an easily observable shift in mass is detectable. Variables that affect the stability of loaded cages include NaCl concentration (100-500 mM), the extent of scaffold saturation (50-100%), total protein concentration, and the length of the loading reaction. As illustrated in FIG. 1A, the PyPABP1:nanocage interaction is strong and successful at both 1:1 and 1:2 molar ratios allowing near full saturation of the nanocage with PyPABP1. FIG. 1B illustrates the binding of 2×AP2 to nanocages at various molar ratios where intact bound nanocages are readily observed at all concentrations tested. For 2×AP2, the binding to the nanocage was performed at 500 mM NaCl illustrating successful saturation at relatively high salt concentrations. FIG. 1C illustrates selective binding of target protein TTP to nanocages. When performed at 100 mM NaCl concentration in the reaction buffer near full saturation of the nanocages is observed. As illustrated in FIG. 1D, UIS12 RRM are readily formed. The target bound nanocages were also subjected to a 2 hour incubation at RT in 100 mM NaCl at the various concentrations. As is shown in the right panel of FIG. 1D at about 50% saturation, the interaction between the nanocages and the target protein are stable.

Example 4

The empty nanocages (no target protein bound, but may have the capture sequence and a linker) formed as in Example 1 are studied by transmission electron microscopy (TEM) or cryo-EM to obtain structural information about the nanocages. For TEM, 3 µL of sample is applied to a carbon-coated 300-mesh grid and stained with neutral 0.3% phosphotungstic acid. The samples are assessed for purity, stability, and concentration with a Tecnai G2 Spirit BioTwin operated at 120 kV. For cryo-EM, 3 µL of sample is applied three times to a 2/1 copper Quantifoil grid and manually botted after the first and second application. After the third application, the quantifoil is blotted for 3 seconds at −10 blot force and plunge frozen in liquid ethane with a Vitribot freezing robot. High-resolution cryo-EM data is collected on a Titan Krios at 300 kV with either the Falcon III or K2 direct electron detector. Micrographs are typically collected at a magnification that results in a pixel size of 1.013 or 1.136 Angstroms per pixel. Micrographs are motion and CTF corrected with MotionCor2 (Zheng, et al, *Nature Methods,* 2016, submitted. BioArxiv:http://biorxiv.org/content/early/2016/07/04/061960) and GCTF (Zhang, *J. Struct. Biol.,* 2016; 193(1): 1-12), respectively. Particles are then selected, extracted, classified, and refined through RELION/ 2.1 (Scheres, *J. Struct. Biol.,* 2012; 193(1): 1-12), using the model of the scaffold cage as an input reference model (Hsia, et al., *Nature,* 2016; 535:136-139). Healpix order must be 5, not the default of 2, during 3D classification for appropriate global alignment of the scaffold to occur.

Figure 2A:
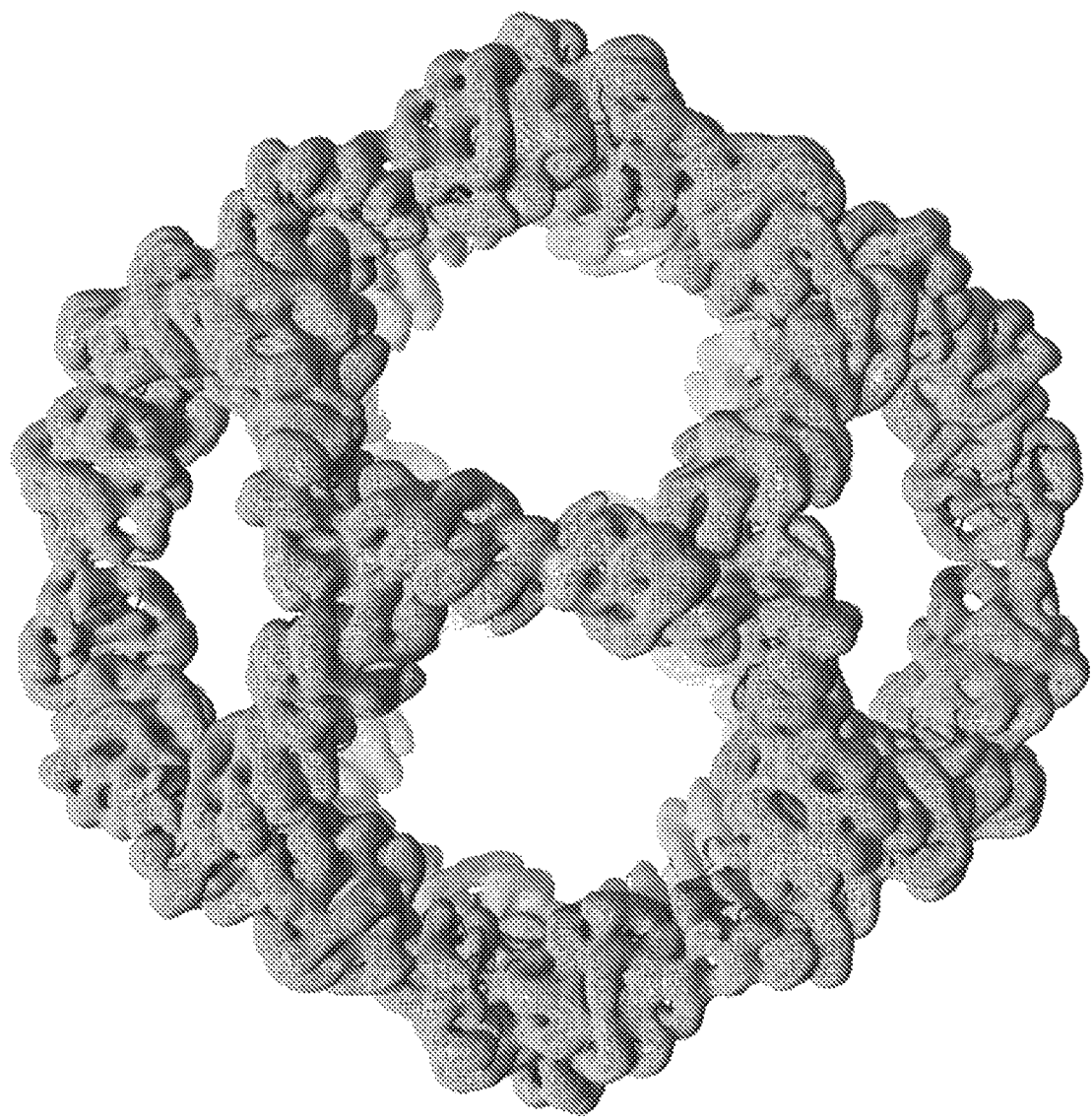
FIG. 2A illustrates the empty nanocage with no linker or capture sequence at 7.64 Å resolution by Cryo-EM.
Figure 2B:
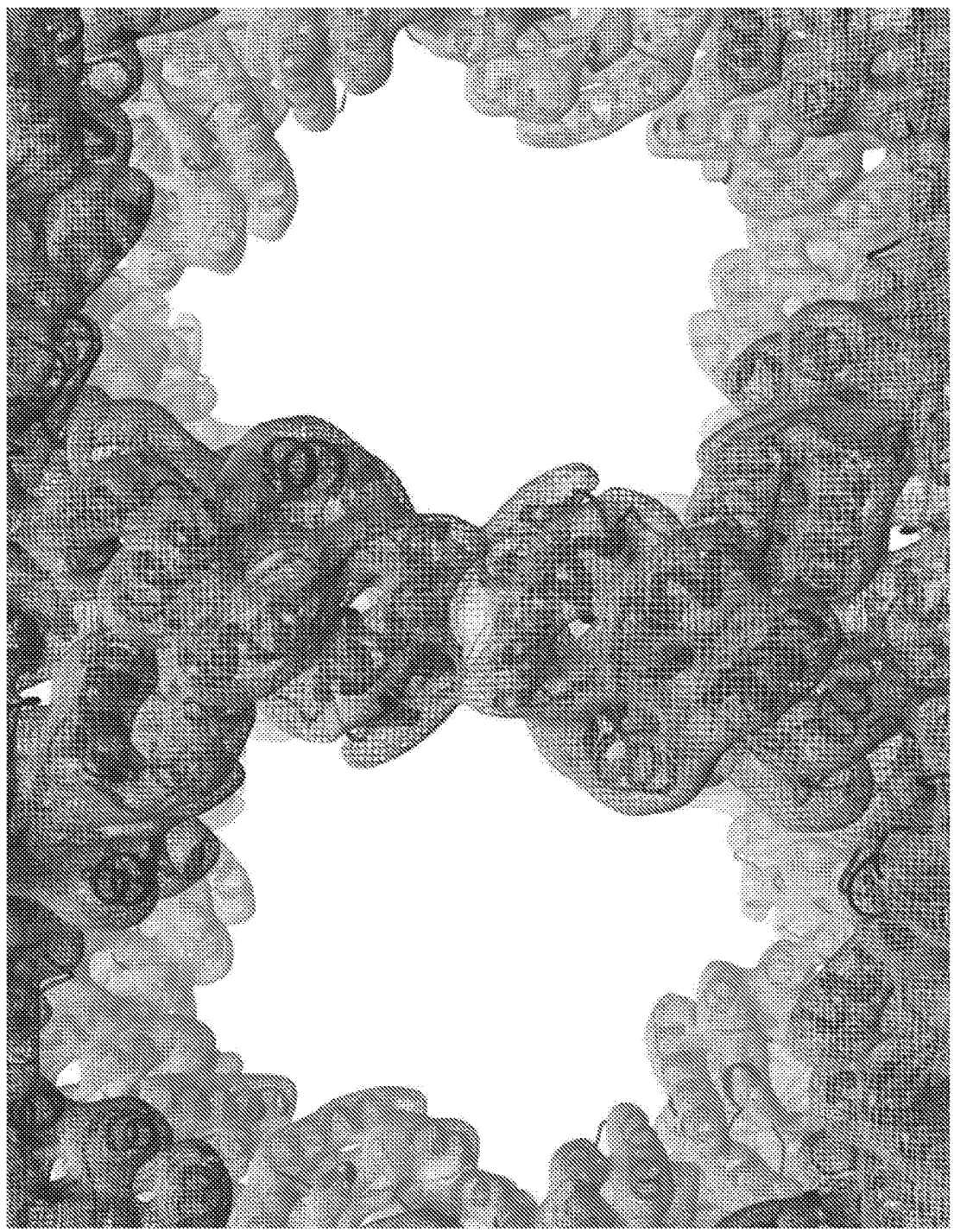
FIG. 2B illustrates a zoomed in view of the empty nanocage of FIG. 2A illustrating resolvable secondary structure and substructure interaction.
Figure 3:
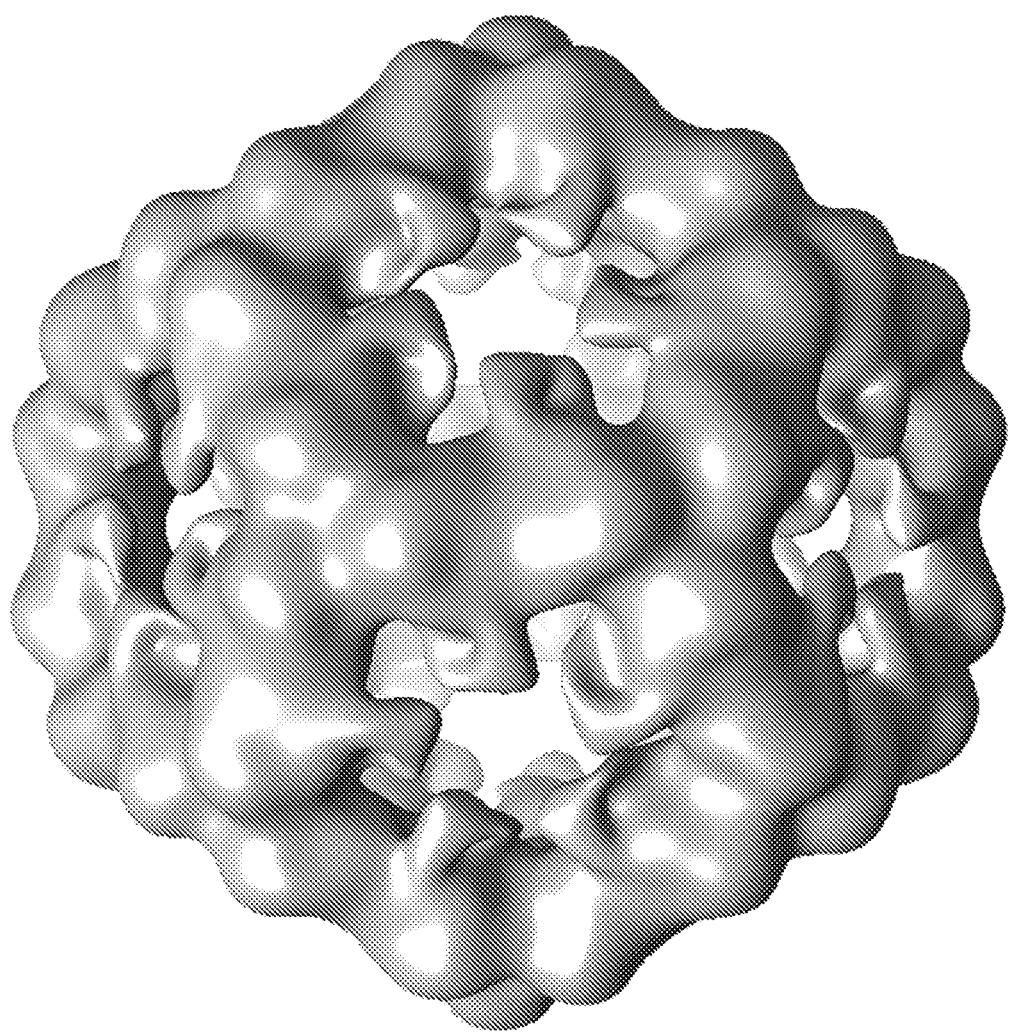
FIG. 3 illustrates a Cryo-EM 3D reconstruction of a nanocage with a flexible 4×GGS linker positioned between the N-terminus of each substructure protein and a capture sequence.

The cryo-EM structure of the empty nanocage is illustrated in FIGS. 2A and 2B demonstrating sufficient resolution to observe secondary structure as well as substructure protein interactions. The nanocage of Example 1 with a fused capture sequence of PDB accession number is 4MLS linked to the N-termini of each of the substructure proteins was similarly analyzed by cryo-EM with the results illustrated in FIG. 3. The flexible linker being a 4-mer repeat of GGS was introduced between the capture sequence and the substructure proteins. The reconstruction was solved to a resolution of about 15 Å. In this instance, the flexible linker moves the capture sequence density toward the 5-fold face of the cages.

Figure 4:
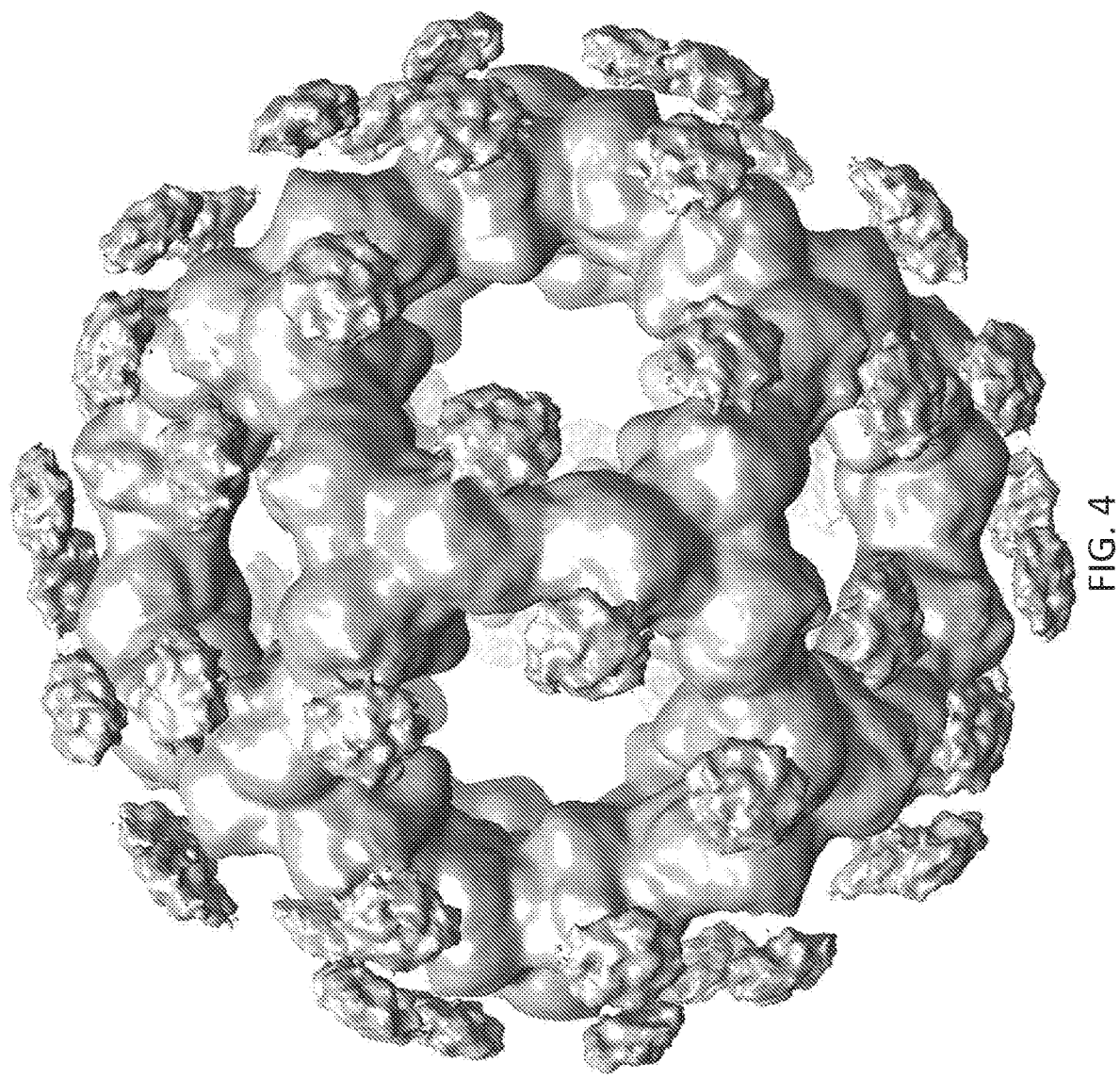
FIG. 4 illustrates a Cryo-EM 3D reconstruction of a nanocage with a rigid 3×PPA linker positioned between the N-terminus of each substructure protein and a capture sequence.
Figure 5:
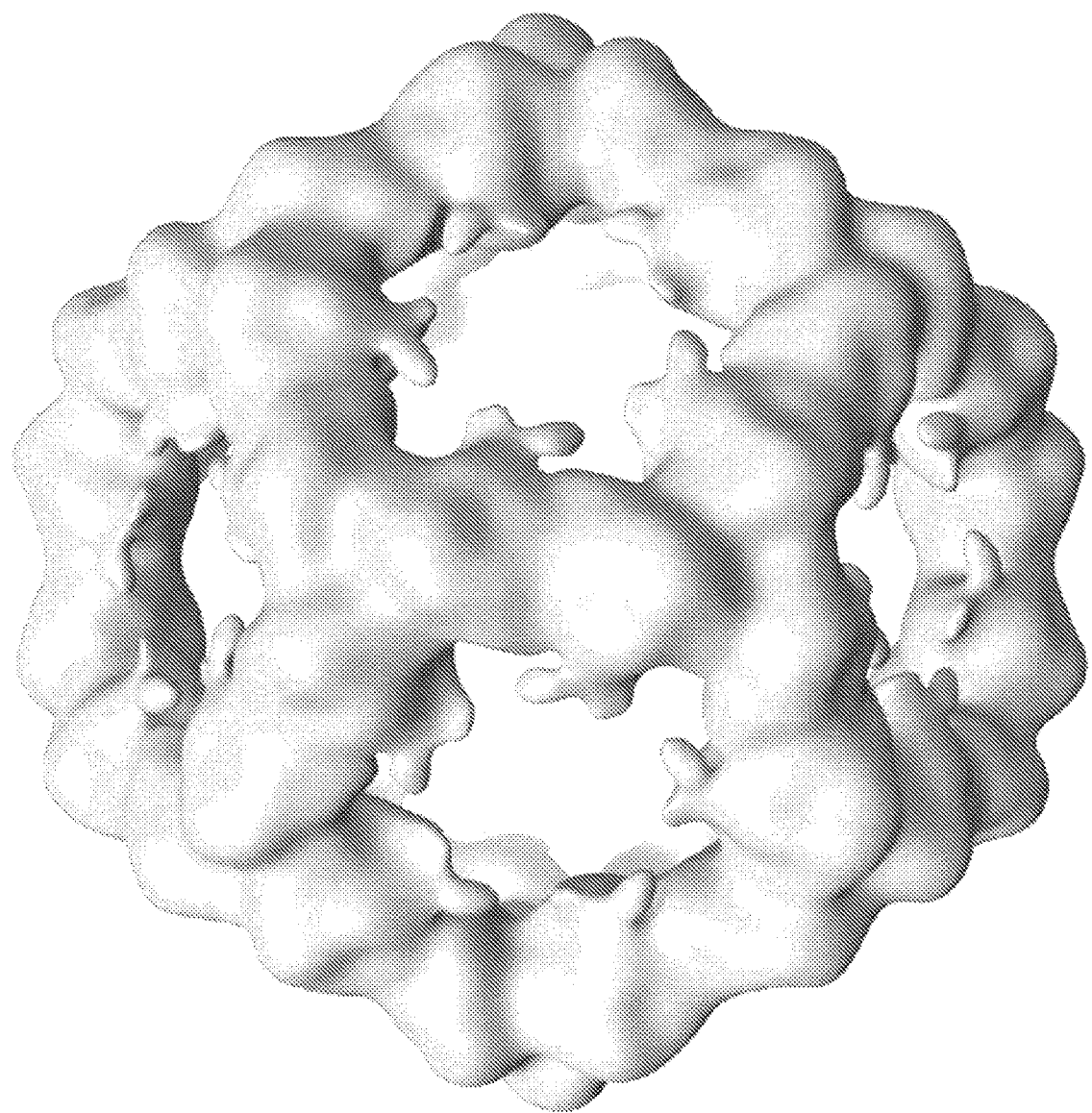
FIG. 5 illustrates a Cryo-EM 3D reconstruction of a nanocage with a flexible GGS linker positioned between the N-terminus of each substructure protein and a capture sequence with the nanocage with a resolution of 15 Å, bound to cytosolic *Plasmodium yoelii* Poly-A Binding Protein (PABP).

Replacing the flexible 4×GGS linker with a rigid 3×PPA linker resulted in the capture domain sequence density outward from the scaffold for excellent association with any desired target protein displaying a suitable tag that can associate with the capture sequence. The results of the cryo-EM are illustrated in FIG. 4.

The exemplary target protein cytosolic Poly-A Binding Protein (PABP) with a tag complementary to the capture sequence was bound to the nanocage including a flexible 4×GGS linker and the solution structure solved by cryo-EM as above. The resulting 15 Å resolution map reveals non-cage density consistent with additional capture domain and target protein densities.

Various modifications of the present invention, in addition to those shown and described herein, will be apparent to those skilled in the art of the above description.

It is appreciated that all reagents used in the manufacture or use of the materials of the present disclosure are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The invention claimed is:

1. A process of solving a three-dimensional structure of a target protein comprising:
   non-genetically associating a target protein with a preformed multimeric self-assembling protein structure to form a target complex, wherein the multimeric self-assembling protein structure comprises a plurality of protein substructures, wherein each of the protein substructures comprises an amino acid sequence that is 70% or greater identical to any one of SEQ ID NOs: 1-6, and
   subjecting said target complex to cryo-electron microscopy whereby the multimeric self-assembling protein structure serves as a scaffold for solution of a three-dimensional structure of said target protein, optionally wherein said target protein has a molecular weight of 200 kilodaltons or less, and optionally a value of resolution of said three-dimensional structure is less than 20 angstroms.

2. The process of claim 1 wherein one or more of said protein substructures comprises a capture sequence, the capture sequence expressed at the N-terminus of the protein substructure or within 10 amino acids from the N-terminus of the protein substructure.

3. The process of claim 1 wherein one or more of said protein substructures comprises a linker and a capture sequence, the linker covalently bonding the capture sequence to the protein substructure.

4. The process of claim 1 wherein each of said protein substructures comprises an amino acid sequence that is identical to any one of SEQ ID NOs: 1-6.

5. The process of claim 1 wherein one or more of the protein substructures comprises a capture sequence, the capture sequence expressed at or near the N-terminus of the protein substructure, the capture sequence comprising the sequence of SEQ ID NO: 8, SEQ ID NO: 9, biotin, or avidin.

6. The process of claim 1 wherein one or more of said protein substructures comprises a linker and a capture sequence, the linker covalently bonding the capture sequence to the protein substructure, the linker a flexible linker or a rigid linker.

7. The process of claim 6 wherein the multimeric self-assembling protein structure is a 60-mer or forms a dodecahedron.

8. The process of claim 1 wherein the target protein has a molecular weight of less than 200 kDa.

9. The process of claim 1 wherein the target protein comprises a tag, the tag suitable for high affinity binding to a capture sequence on the multimeric self-assembling protein structure, the tag optionally comprising SEQ ID NO: 20, SEQ ID NO: 21, biotin, or avidin.

10. The process of claim 1 wherein said multimeric self-assembling protein structure to form a target complex is in an aqueous buffer comprising at or greater than 100 mM of a salt.

11. The process of claim 1 wherein said value of resolution is less than 10 Å.

* * * * *